US011591616B1

(12) United States Patent
MacNeill et al.

(10) Patent No.: US 11,591,616 B1
(45) Date of Patent: Feb. 28, 2023

(54) APOPTOTIC UPREGULATION BY MYXOMA VIRUS EXPRESSING WALLEYE DERMAL SARCOMA VIRUS ORFC

(71) Applicants: Amy MacNeill, Bellvue, CO (US); Sandra Quackenbush, Fort Collins, CO (US); Laura Ashton, Loveland, CO (US)

(72) Inventors: Amy MacNeill, Bellvue, CO (US); Sandra Quackenbush, Fort Collins, CO (US); Laura Ashton, Loveland, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 463 days.

(21) Appl. No.: 16/855,115

(22) Filed: Apr. 22, 2020

Related U.S. Application Data

(60) Provisional application No. 62/837,020, filed on Apr. 22, 2019.

(51) Int. Cl.
*C12N 15/86* (2006.01)
*A61K 35/768* (2015.01)
*A61K 38/16* (2006.01)
*A61P 35/00* (2006.01)
*C12N 7/00* (2006.01)

(52) U.S. Cl.
CPC ............ *C12N 15/86* (2013.01); *A61K 35/768* (2013.01); *A61K 38/16* (2013.01); *A61P 35/00* (2018.01); *C12N 7/00* (2013.01); *C12N 2710/24032* (2013.01); *C12N 2710/24043* (2013.01); *C12N 2740/10033* (2013.01); *C12N 2740/10071* (2013.01)

(58) Field of Classification Search
CPC ............ C12N 2710/24032; C12N 7/00; C12N 2710/24071; C12N 2710/24033; C12N 2750/14143; C12N 2740/16043; C12N 2710/24171; C12N 2710/24132; C12N 2710/16662; C12N 2710/16671; C12N 2710/24051; C12N 2710/24045; C12N 2740/10043; C12N 15/113; C12N 2710/24243; C12N 15/86; C12N 2740/15043; C12N 2740/15071; C12N 2750/14171; C12N 9/93; C12N 15/111; C12N 15/67; A61P 19/04; A61K 48/005; A61K 38/00; C07K 14/50; C07K 14/47; C12Y 601/01002; C12Y 601/01004; C12Y 601/01026; C12Y 601/01001; C12P 21/02
See application file for complete search history.

(56) References Cited

U.S. PATENT DOCUMENTS 8,227,440 B2  7/2012  McFadden et al.
2021/0169957 A1  6/2021  Kim
2021/0196771 A1  7/2021  Kiefer et al.

FOREIGN PATENT DOCUMENTS

WO  2001004318 A2  1/2001

OTHER PUBLICATIONS

Fenner, F. Adventures with poxviruses of vertebrates. FEMS Microbiol. Rev. 2000, 24, 123-133.
McCabe, V.J.; Tarpey, I.; Spibey, N. Vaccination of cats with an attenuated recombinant myxoma virus expressing feline calicivirus capsid protein. Vaccine 2002, 20, 2454-2462.
McCabe, V.J.; Spibey, N. Potential for broad-spectrum protection against feline calicivirus using an attenuated myxoma virus expressing a chimeric FCV capsid protein Vaccine 2005, 23, 5380-5388.
MacNeill, A.L.; Moldenhauer, T.; Doty, R.; Mann, T. Myxoma virus induces apoptosis in cultured feline carcinoma cells. Res. Vet. Sci. 2012, 93, 1036-1038.
Condit, R.C.; Motyczka, A. Isolation and preliminary characterization of temperature-sensitive mutants of vaccinia virus. Virology 1981, 113, 224-241.
Pol, J., Kroemer, G., & Galluzzi, L. (2015). First oncolytic virus approved for melanoma immunotherapy Oncoimmunology, 5(1), e1115641. https://doi.org/10.1080/2162402X.2015.1115641.
Andrewes CH, Harisijades S. Propagation of myxoma virus in one-day old mice. Br J Exp Pathol. 1955;36 (1):18-21.
Fenner, F., & Woodroofe, G. M. (1953). The pathogenesis of infectious myxomatosis; the mechanism of infection and the immunological response in the European rabbit (*Oryctolagus cuniculus*). British journal of experimental pathology, 34(4), 400-411.
Górski J, Mizak B, Chrobocińska M. Control of rabbit myxomatosis in Poland. Rev Sci Tech. 1994;13(3):869-879. doi:10.20506/rst.13.3.803.
Jackson, E., Dorn, C., Saito, J. et al. Absence of Serological Evidence of Myxoma Virus Infection in Humans exposed during an Outbreak of Myxomatosis. Nature 211, 313-314 (1966).
Pignolet B, Boullier S, Gelfi J, et al. Safety and immunogenicity of myxoma virus as a new viral vector for small ruminants. J Gen Virol. 2008;89(Pt6):1371-1379. doi:10.1099/vir.0.83595-0.
Urbasic AS, Hynes S, Somrak A, et al. Oncolysis of canine tumor cells by myxoma virus lacking the serp2 gene. Am J Vet Res. 2012;73(8):1252-1261. doi:10.2460/ajvr.73.8.1252.
Wang F, Ma Y, Barrett JW, et al. Disruption of Erk-dependent type I interferon induction breaks the myxoma virus species barrier. Nat Immunol. 2004;5(12):1266-1274. doi:10.1038/ni1132.

(Continued)

*Primary Examiner* — Bao Q Li
(74) *Attorney, Agent, or Firm* — Michael M. McGaw; McGaw Law, P.C.

(57) ABSTRACT

A recombinant myxoma virus that encodes the orfC gene of walleye dermal sarcoma virus (WDSV). The orfC gene of walleye dermal sarcoma virus (WDSV) plays a role in induction of seasonal regression of tumors caused by WDSV. This gene was isolated from WDSV and recombined into myxoma virus (MYXV orfC) for use as an oncolytic therapy. The recombinant myxoma virus can be used in oncolytic virus therapy to specifically target and lyse cancer cells without harming healthy cells in cancer patients.

8 Claims, 17 Drawing Sheets

(56) References Cited

OTHER PUBLICATIONS

Woo, Y., Kelly, K.J., Stanford, M.M. et al. Myxoma Virus Is Oncolytic for Human Pancreatic Adenocarcinoma Cells. Ann Surg Oncol 15, 2329-2335 (2008). https://doi.org/10.1245/s10434-008-9924-z.

Wang G, Barrett JW, Stanford M, et al. Infection of human cancer cells with myxoma virus requires Akt activation via interaction with a viral ankyrin-repeat host range factor. Proc Natl Acad Sci U S A. 2006;103(12):4640-4645. doi:10.1073/pnas.0509341103.

Bartee, E., & McFadden, G. (2009). Human cancer cells have specifically lost the ability to induce the synergistic state caused by tumor necrosis factor plus interferon-beta. Cytokine, 47(3), 199-205. https://doi.org/10.1016/j.cyto.2009.06.006.

Lun X, Yang W, Alain T, et al. Myxoma virus is a novel oncolytic virus with significant antitumor activity against experimental human gliomas Cancer Res. 2005;65(21):9982-9990. doi:10 1158/0008-5472.CAN-05-1201.

Lun X, Alain T, Zemp FJ, et al. Myxoma virus virotherapy for glioma in immunocompetent animal models: optimizing administration routes and synergy with rapamycin. Cancer Res. 2010;70(2):598-608. doi:10.1158/0008-5472.CAN-09-1510.

Stanford, M. M., Shaban, M., Barrett, J. W., Werden, S. J., Gilbert, P. A., Bondy-Denomy, J., Mackenzie, L., Graham, K. C., Chambers, A. F., & McFadden, G. (2008). Myxoma virus oncolysis of primary and metastatic B16F10 mouse tumors in vivo Molecular therapy : the journal of the American Society of Gene Therapy, 16(1), 52-59. https://doi.org/10.1038/sj.mt.6300348.

Thomas DL, Doty R, Tosic V, et al. Myxoma virus combined with rapamycin treatment enhances adoptive T cell therapy for murine melanoma brain tumors. Cancer Immunol Immunother. 2011;60(10):1461-1472. doi:10.1007/s00262-011-1045-z.

Doty RA, Liu J, McFadden G, Roy EJ, MacNeill AL. Histological evaluation of intratumoral myxoma virus treatment in an immunocompetent mouse model of melanoma. Oncolytic Virother. 2013;2:1-17. doi:10.2147/OV.S37971.

Nudson WA, Rovnak J, Buechner M, Quackenbush SL. Walleye dermal sarcoma virus Orf C is targeted to the mitochondria. J Gen Virol. 2003;84(Pt 2):375-381. doi:10.1099/vir.0.18570-0.

Liu, J., Wennier, S., Reinhard, M., Roy, E., MacNeill, A., & McFadden, G. (2009). Myxoma virus expressing interleukin-15 fails to cause lethal myxomatosis in European rabbits. Journal of virology, 83(11), 5933-5938. https://doi.org/10.1128/JVI.00204-09.

Rice, A. D., Gray, S. A., Li, Y., Damon, I., & Moyer, R. W. (2011). An efficient method for generating poxvirus recombinants in the absence of selection. Viruses, 3(3), 217-232. https://doi.org/10.3390/v3030217.

Rice, A. D., Adams, M. M., Lindsey, S. F., Swetnam, D. M., Manning, B. R., Smith, A. J., Burrage, A. M., Wallace, G., MacNeill, A. L., & Moyer, R. W. (2014). Protective properties of vaccinia virus-based vaccines: skin scarification promotes a nonspecific immune response that protects against orthopoxvirus disease. Journal of virology, 88(14), 7753-7763. https://doi.org/10.1128/JVI.00185-14.

Kinn, V. G., Hilgenberg, V. A., & MacNeill, A. L. (2016). Myxoma virus therapy for human embryonal rhabdomyosarcoma in a nude mouse model. Oncolytic virotherapy, 5, 59-71. https://doi.org/10.2147/OV.S108831.

MacNeill AL, Turner PC, Moyer RW. Mutation of the Myxoma virus SERP2 P1-site to prevent proteinase inhibition causes apoptosis in cultured RK-13 cells and attenuates disease in rabbits, but mutation to alter specificity causes apoptosis without reducing virulence. Virology. 2006;356(1-2):12-22. doi:10.1016/j.virol.2006.07.049.

MacNeill, A. L., Weishaar, K. M., Séguin, B., & Powers, B. E. (2018). Safety of an Oncolytic Myxoma Virus in Dogs with Soft Tissue Sarcoma. Viruses, 10(8), 398. https://doi.org/10.3390/v10080398.

```
┌─────────────────┐
│ Isolate the orfC│
│ gene from WDSV &│      ┌──────────────────────┐
│ add a hemagglutinin│──▶│ Evaluate MYXV orfC   │
│ tag (HA-orfC)   │      │ replication rate in  │
└────────┬────────┘      │ permissive RK13 cells│
         ▼               └──────────────────────┘
┌─────────────────┐      ┌──────────────────────┐
│ Recombine HA-orfC│────▶│ Perform a Western blot to│
│ & tomato red genes│    │ confirm HA-orfC production│
│ into MYXV       │      └──────────────────────┘
└────────┬────────┘      ┌──────────────────────┐
         │               │ Infect canine cancer cells│
         │               │ with MYXV orfC or    │
         │          ◀────│ MYXV red to assess   │
         ▼               │ effects in cell culture│
┌─────────────────┐      └──────────┬───────────┘
│ Look for virus  │                 │
│ replication & protein│            │
│ expression using tomato│          │
│ red fluorescence│                 │
└────────┬────────┘                 │
         ▼                          ▼
┌─────────────────┐      ┌──────────────────────┐
│ Look for cell viability│ Detect phosphatidylserine on│
│ using a luciferase assay│ apoptotic cells using│
└────────┬────────┘      │ luciferase-labeled Annexin V│
         │               └──────────┬───────────┘
         ▼                          ▼
      ┌──────────────────────────────────┐
      │ Compile data to characterize MYXV │
      │ orfC infection of canine cancer cells│
      └──────────────────────────────────┘
```

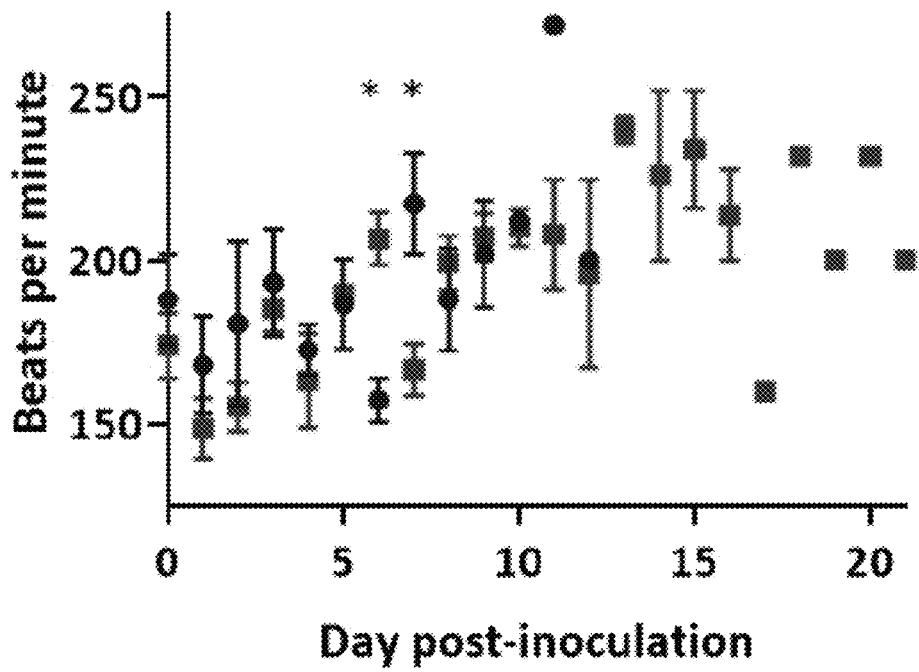
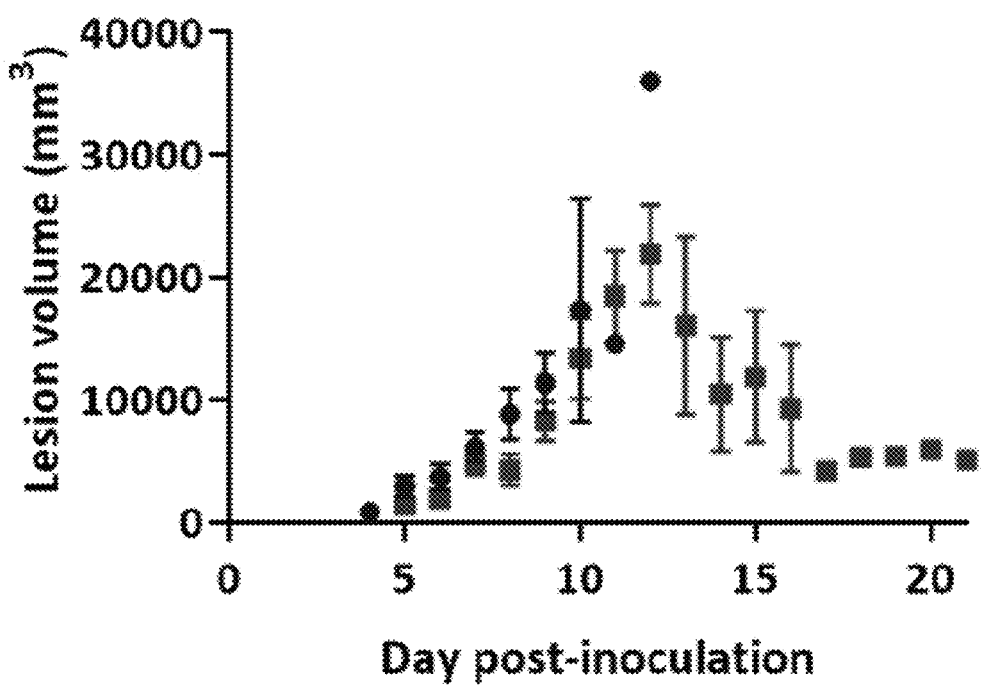
FIG. 11 - continued

FIG. 12

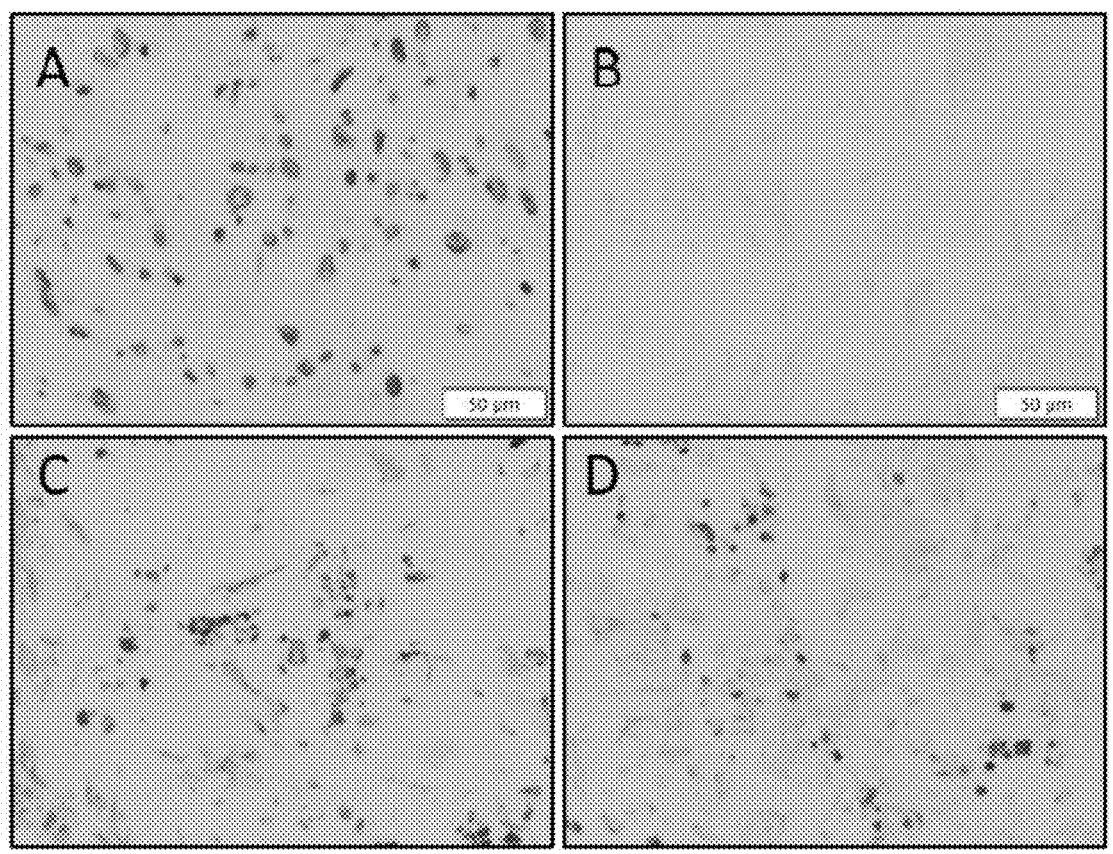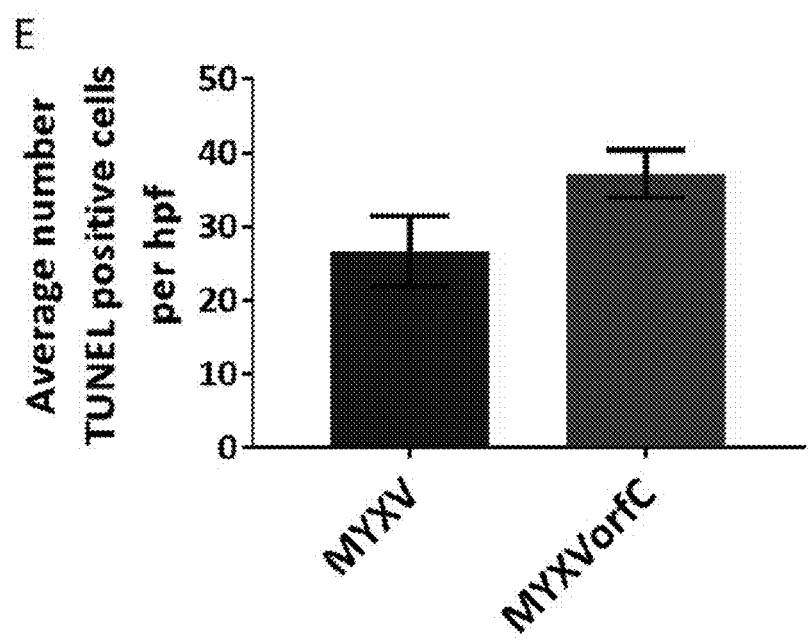
FIG. 14

APOPTOTIC UPREGULATION BY MYXOMA VIRUS EXPRESSING WALLEYE DERMAL SARCOMA VIRUS ORFC

CROSS-REFERENCE TO RELATED APPLICATIONS

This application claims the benefit of U.S. Provisional Application No. 62/837,020, filed Apr. 22, 2019.

FIELD OF INVENTION

This invention relates to oncolytic viral therapy. More particularly, the present invention relates to the apoptotic upregulation of recombinant oncolytic viruses by the expression of the orfC gene of walleye dermal sarcoma virus from the recombinant oncolytic virus.

BACKGROUND OF THE INVENTION

There is a growing interest in using viruses to eliminate cancers. The first oncolytic virus (OV) approved for use in the United States is marketed for treatment of melanoma in humans [Pol, J.; Kroemer, G.; Galluzzi, L. First oncolytic virus approved for melanoma immunotherapy. *Oncoimmunology* 5, e1115641]. Although there are ongoing clinical trials testing the efficacy of oncolytic virotherapy in many types of human cancers, new OVs that are safer and more globally effective are actively being researched.

SUMMARY OF THE INVENTION

Oncolytic virus therapy uses a replicating virus to specifically target and lyse cancer cells without harming healthy cells in cancer patients. The orfC gene of walleye dermal sarcoma virus (WDSV) encodes a pro-apoptotic protein thought to induce seasonal regression of tumors caused by WDSV. This gene was isolated from WDSV and recombined into myxoma virus (MYXV orfC) for use as an oncolytic therapy. Expression of orfC during treatment with MYXV orfC enhances apoptosis of infected cancer cells. Cells were inoculated with MYXV orfC, wild-type MYXV, or MYXV expressing a red fluorescent protein (MYXV red) at a multiplicity of infection (moi) of 1. Virus growth rate in rabbit kidney epithelial (RK-13) cells was similar for all viruses. Cell viability and morphology following infection with MXYV OrfC or MYXV red was similar at several time-points after infection. An important difference between viruses was the higher levels of apoptosis expressed in the cell lines infected with MYXV orfC. The data presented herein indicates that MYXV orfC is capable of infecting various canine cancer cell cultures and enhances apoptosis in the cells as compared to MYXV infection. The increased apoptosis observed with MYXV orfC could improve the oncolytic effects of the virus in cancer patients.

In a first aspect the present invention provides a recombinant myxoma virus that encodes the orfC gene of walleye dermal sarcoma virus (WDSV). It is found that the inclusion of the orfC gene significantly enhances the apoptotic effect of the myxoma virus, thereby making it a more effective anti-cancer agent when compared to a myxoma virus lacking the orfC gene. The orfC gene of walleye dermal sarcoma virus can be inserted between M135 and M136 open reading frames of the myxoma virus genome. The orfC gene of walleye dermal sarcoma virus can be expressed under the control of the late poxvirus promoter (p11). In an advantageous embodiment the myxoma virus is an attenuated myxoma virus.

In a second aspect the present invention provides a method of killing a cancer cell comprising the step of contacting the cell with a recombinant myxoma virus that encodes the orfC gene of walleye dermal sarcoma virus (WDSV). In an advantageous embodiment the cell is a mammalian cancer cell. In further embodiments the cancer cell is a human cancer cell.

In a third aspect the present invention provides a method of treating or preventing cancer in a subject comprising the step of administering to the subject a therapeutically effective amount of a recombinant myxoma virus that encodes the orfC gene of walleye dermal sarcoma virus (WDSV). Advantageously, between about $10^2$ and $10^9$ pfu of the virus is administered to the subject. In an advantageous embodiment the method can further include the step of delivering to the subject an additional cancer therapy. Examples of additional cancer therapies include surgery, radiation, chemotherapy, immunotherapy, hormone therapy, and combinations thereof.

In a fourth aspect the present invention provides a recombinant oncolytic virus for anti-cancer therapy comprising a recombinant oncolytic virus that encodes the orfC gene of walleye dermal sarcoma virus (WDSV). The recombinant oncolytic virus for anti-cancer therapy of the fourth aspect can be a virus from one of the following virus families: Parvoviridae, Poxviridae, Paramyxoviridae, Reoviridae, Picornaviridae, Paramyxoviridae, Adenoviridae, Herpesviridae, and Rhabdoviridae. In an advantageous embodiment the recombinant oncolytic virus of the fourth aspect is a virus selected from the group consisting of myxoma virus, Newcastle disease virus, reovirus, and Seneca valley virus, measles virus, poliovirus, vaccinia virus, adenovirus, herpes simplex virus (e.g. HSV1), and vesicular stomatitis virus. The recombinant oncolytic virus having the orfC gene of walleye dermal sarcoma virus can be expressed under the control of a late poxvirus promoter (p11).

In a fifth aspect the present invention provides a method of killing a cancer cell comprising contacting the cell with the recombinant oncolytic virus that encodes the orfC gene of walleye dermal sarcoma virus (WDSV).

In a sixth aspect the present invention provides a method of treating or preventing cancer in a subject comprising the step of administering to the subject a therapeutically effective amount of the recombinant oncolytic virus that encodes the orfC gene of walleye dermal sarcoma virus (WDSV). Advantageously, between about $10^2$ and $10^9$ pfu of the virus is administered to the subject. In an advantageous embodiment the method according to the sixth aspect can further include the step of delivering to the subject an additional cancer therapy. Examples of additional cancer therapies include surgery, radiation, chemotherapy, immunotherapy, hormone therapy, and combinations thereof.

BRIEF DESCRIPTION OF THE DRAWINGS

For a fuller understanding of the invention, reference should be made to the following detailed description, taken in connection with the accompanying drawings, in which:

FIG. 1 is a flowchart showing the steps performed to create MYXV orfC.

FIG. 3A is an illustration/diagram showing a DNA fragment from MYXV orfC with inserted genes (2385 bp). Lighter gray regions (upper bar indicating base pair regions) were sequenced using Sanger sequencing. No unwanted mutations were detected. The illustration provides a linear map of MYXV OrfC after recombination of OrfC and tdTomato into wild-type MYXV.

FIG. 3B is an alignment of purified recombinant MYXVorfC DNA compared to MYXV (A1170726.2) using next generation sequencing. The expected PCR insert was successfully recombined into MYXV to create MYXVorfC. Wild-type MYXV sequence was not detected in the purified MYXVorfC virus sample.

FIG. 4 is a graph showing that MYXV replication is not altered by tomato red & orfC gene inserts. The upper plot at the t=50 hour timepoint is "Average MYXV orfC". The middle plot at the t=50 hour timepoint is "Average MYXV red". The lower plot at the t=50 hour timepoint is "Average MYXV".

FIG. 7 is an image showing a Western immunoblot. Hemagglutinin-tagged orfC was detected in RK-13 cell lysates by 12 hours post-infection (moi=0.5).

FIG. 10 is a pair of graphs showing differences in disease progression in rabbits after intradermal inoculation of 50 pfu MYXV or MYXVorfC. (A) Average daily clinical score (error bars=SEM, *p-values<0.05). (B) Day that development of primary and secondary skin lesions was first observed on individual rabbits.

FIG. 11 is a set of four graphs showing average daily measurements during physical examination of rabbits infected with 50 pfu of MYXV or MYXVorfC. Small, but statistically significant differences were observed on a few days when average (A) body temperature, (B) respiratory rate, and (C) heart rate were compared. No significant differences were observed when (D) average daily lesion volumes were calculated (error bars=SEM, p-values<0.05).

FIG. 12 is a graph showing the average virus titer in rabbit tissues. Tissue homogenates from MYXV- and MYXVorfC-infected rabbits at the time of euthanasia contained replicating virus. Significantly lower titers of MYXVorfC were extracted from primary lesions, lung, and spleen (error bars=SEM, *p-values<0.05).

FIG. 14 is a set of four photomicrographs (A-D) and a graph (E) showing TUNEL staining in primary skin lesions. (A) Positive (brown nuclei) and (B) negative control samples were adequate. Positive TUNEL staining was observed in both (C) MYXV-infected and (D) MYXVorfC-infected rabbits. (E) The average number of TUNEL positive cells in ten 40× objective high-power fields (hpf) was calculated. The difference between TUNEL staining in primary lesions of MYXV- and MYXVorfC-infected rabbits was not statistically significant.

DETAILED DESCRIPTION OF THE PREFERRED EMBODIMENT

Figure 2A:
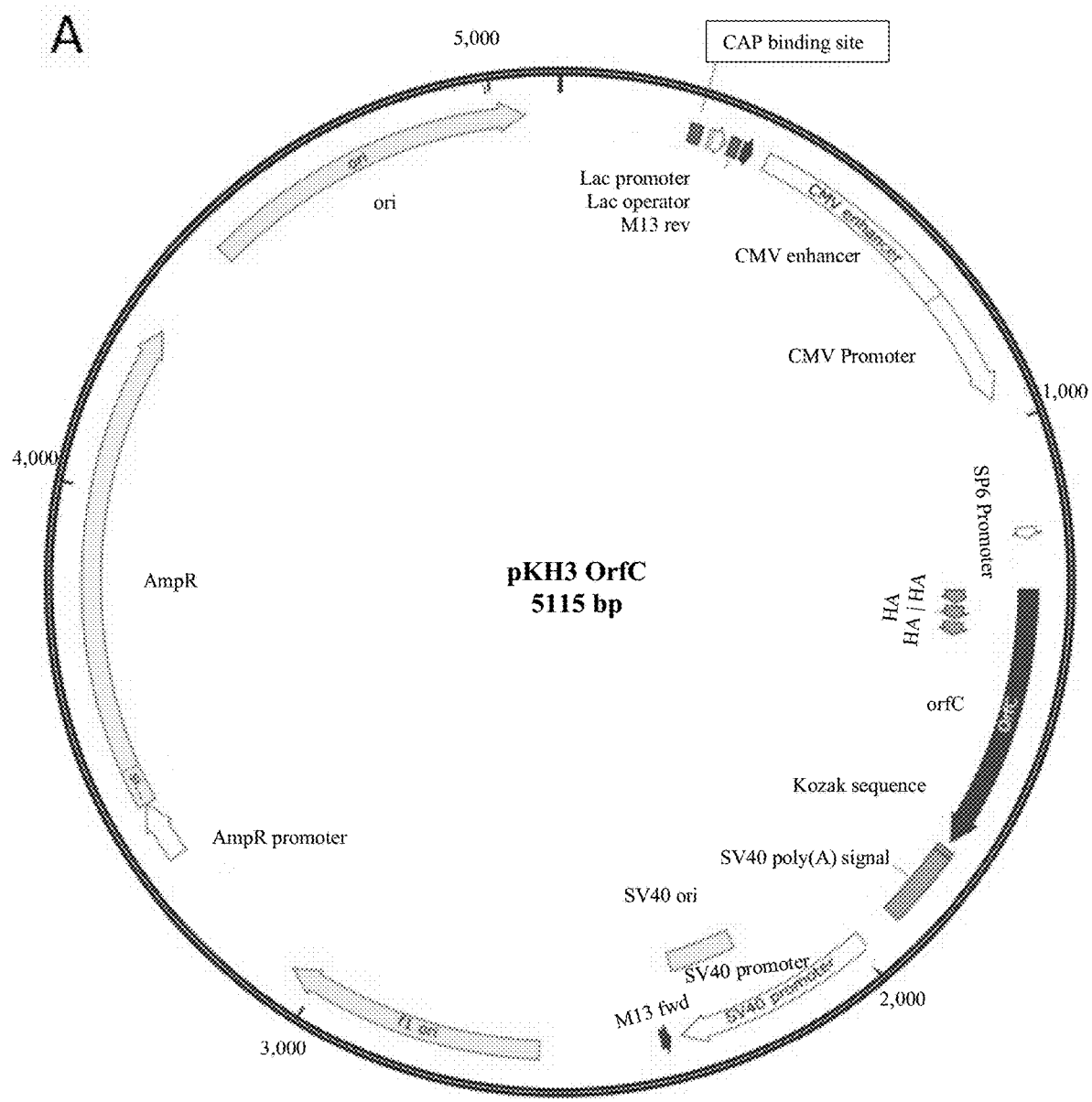
FIG. 2A is a plasmid map of HA-tagged orfC [Nudson, W. A.; Rovnak, J.; Buechner, M.; Quackenbush, S. L. Walleye dermal sarcoma virus Orf C is targeted to the mitochondria. *J. Gen. Virol.* 2003, 84, 375-381.].

The poxvirus, MYXV is an excellent candidate oncolytic virotherapeutic because, unlike other OVs, it does not cause disease in humans or other vertebrates, with the exception of rabbits [Gorski, J.; Mizak, B.; Chrobocinska, M. Control of rabbit myxomatosis in Poland. Rev. Sci. Tech. 1994, 13, 869-879; Jackson, E. W.; Dorn, C. R.; Saito, J. K.; McKercher, D. G. Absence of serological evidence of myxoma virus infection in humans exposed during an outbreak of myxomatosis. Nature 1966, 211, 313-314.]. In spite of its species specificity, MYXV productively infects cultured cancer cells from several animal species [MacNeill, A. L.; Moldenhauer, T.; Doty, R.; Mann, T. Myxoma virus induces apoptosis in cultured feline carcinoma cells. Res. Vet. Sci. 2012, 93, 1036-1038; Urbasic, A. S.; Hynes, S.; Somrak, A.; Contakos, S.; Rahman, M. M.; Liu, J.; MacNeill, A. L. Oncolysis of canine tumor cells by myxoma virus lacking the serp2 gene. Am. J. Vet. Res. 2012, 73, 1252-1261; Wang, F.; Ma, Y.; Barrett, J. W.; Gao, X.; Loh, J.; Barton, E.; Virgin, H. W.; McFadden, G. Disruption of Erk-dependent type I interferon induction breaks the myxoma virus species barrier. Nat. Immunol. 2004, 5, 1266-1274; Woo, Y.; Kelly, K. J.; Stanford, M. M.; Galanis, C.; Chun, Y. S.; Fong, Y.; McFadden, G. Myxoma virus is oncolytic for human pancreatic adenocarcinoma cells. Ann. Surg. Oncol. 2008, 15, 2329-2335.]. In culture, data suggest that MYXV can replicate in neoplastic cells which have activated Akt [Urbasic, A. S.; Hynes, S.; Somrak, A.; Contakos, S.; Rahman, M. M.; Liu, J.; MacNeill, A. L. Oncolysis of canine tumor cells by myxoma virus lacking the serp2 gene. Am. J. Vet. Res. 2012, 73, 1252-1261. Wang, G.; Barrett, J. W.; Stanford, M.;

Werden, S. J.; Johnston, J. B.; Gao, X.; Sun, M.; Cheng, J. Q.; McFadden, G. Infection of human cancer cells with myxoma virus requires Akt activation via interaction with a viral ankyrin-repeat host range factor. *Proc. Natl. Acad. Sci. U.S.A* 2006, 103, 4640-4645.] and lack appropriate Type I interferon responses to virus infection [Wang, F.; Ma, Y.; Barrett, J. W.; Gao, X.; Loh, J.; Barton, E.; Virgin, H. W.; McFadden, G. Disruption of Erk-dependent type I interferon induction breaks the myxoma virus species barrier. *Nat. Immunol.* 2004, 5, 1266-1274; Bartee, E.; McFadden, G. Human cancer cells have specifically lost the ability to induce the synergistic state caused by tumor necrosis factor plus interferon-beta. Cytokine 2009, 47, 199-205.]. In rodent cancer models, MYXV treatment has eliminated some glioma xenografts [Lun, X.; Yang, W.; Alain, T.; Shi, Z. Q.; Muzik, H.; Barrett, J. W.; McFadden, G.; Bell, J.; Hamilton, M. G.; Senger, D. L.; et al. Myxoma virus is a novel oncolytic virus with significant antitumor activity against experimental human gliomas. *Cancer Res.* 2005, 65, 9982-9990.] and reduced tumor burden of different allografts [Thomas, D. L.; Doty, R.; Tosic, V.; Liu, J.; Kranz, D. M.; McFadden, G.; Macneill, A. L.; Roy, E. J. Myxoma virus combined with rapamycin treatment enhances adoptive T cell therapy for murine melanoma brain tumors. Cancer *Immunol. Immunother.* 2011, 60, 1461-1472; Doty, R. A.; McFadden, G.; Roy, E. J.; MacNeill, A. L. Histological evaluation of intratumoral myxoma virus treatment in an immunocompetent mouse model of melanoma. *Oncolytic Virotherapy* 2013, 2, 1-17.], but to date allografts have not been eliminated by MYXV treatment alone. A recombinant MYXV with an enhanced oncolytic effect will be a more potent anti-cancer therapy. However, before a new MYXV OV is tested in cancer models, its safety profile must be determined in its natural host, rabbits, which is shown herein for MYXVorfC.

The pathogenesis of wild-type MYXV compared to a recombinant MYXVorfC virus in New Zealand white rabbits was investigated and the results of that investigation is presented herein. MYXVorfC is associated with an alteration of mitochondrial function that results in apoptosis contributing to tumor regression in fish [orfC from walleye dermal sarcoma virus (WDSV)], [Hudson, W. A.; Rovnak, J.; Buechner, M.; Quackenbush, S. L. Walleye dermal sarcoma virus Orf C is targeted to the mitochondria. *J. Gen. Virol.* 2003, 84, 375-381.]. Data presented herein indicate that MYXVorfC replicates and enhances apoptosis in permissive cell cultures. In rabbits, clinical signs of virus infection are delayed and median survival time is increased in animals inoculated with MYXVorfC as compared to MYXV. One of six rabbits survived infection with MYXVorfC, while all six rabbits infected with MYXV succumbed to disease. These data indicate MYXVorfC is pro-apoptotic in cell culture and is attenuated in rabbits. These properties support using MYXVorfC in animal models of cancer to determine if MYXVorfC is a more effective OV than wild-type MYXV.

Oncolytic virus therapy uses a replicating virus to specifically target and lyse cancer cells without harming any healthy cells in cancer patients. The orfC gene of walleye dermal sarcoma virus (WDSV) plays a role in induction of seasonal regression of tumors caused by WDSV. This gene was isolated from WDSV and recombined into myxoma virus (MYXV orfC) for use as an oncolytic therapy. Expression of orfC during treatment with MYXV orfC will enhance apoptosis of infected cancer cells. Cells were inoculated with MYXV orfC, wild-type MYXV, or MYXV expressing a red fluorescent protein (MYXV red) at a multiplicity of infection (moi) of 1. Virus growth rate in rabbit kidney epithelial (RK-13) cells was similar for all viruses. Cell viability and morphology following infection with MXYV OrfC or MYXV red was similar at several time-points after infection. An important difference between viruses was the higher levels of apoptosis expressed in the cell lines infected with MYXV orfC. The data presented herein indicate that MYXV orfC is capable of infecting various canine cancer cell cultures and enhances apoptosis in the cells as compared to MYXV infection. The increased apoptosis observed with MYXV orfC should improve the oncolytic effects of the virus in cancer patients.

The poxvirus, myxoma virus (MYXV), has shown efficacy as an oncolytic virus (OV) in some cancer models. However, MYXV replication within murine cancer models and spontaneous canine sarcomas is short-lived. In mice, successful treatment of tumors requires frequent injections with MYXV. The present invention provides compositions and methods for the treatment of cancer with a recombinant MYXV that promotes apoptosis and improves the efficacy of MYXV. The orfC gene of walleye dermal sarcoma virus (WDSV), which induces apoptosis, was recombined into the MYXV genome (MYXVorfC). A marked increase in apoptosis was observed in cells infected with MYXVorfC. To ensure that expression of WDSV orfC by MYXV does not potentiate the pathogenesis of MYXV, the effects of MYXVorfC inoculation in the only known host of MYXV, New Zealand white rabbits, was evaluated. Virus dissemination in rabbit tissues was similar for MYXVorfC and MYXV. Virus titers recovered from tissues were lower in MYXVorfC-infected rabbits as compared to MYXV-infected rabbits. Importantly, rabbits infected with MYXVorfC had a delayed onset of clinical signs and a longer median survival time than rabbits infected with MYXV. This indicates that MYXVorfC is attenuated and provides evidence that MYXVorfC will be safe to use as an OV therapy.

Example 1—Materials and Methods

Cell Culture—Rabbit-kidney epithelial (RK-13) cells originated from the kidney of a five-week-old rabbit and were used in the present study. Cell growth media was comprised of Minimal Essential Medium with Earle's salts and 2 mM L-glutamine supplemented with 2 mM L-glutamine, 50 U/mL penicillin, and 50 µg/mL streptomycin (GE Healthcare, Marlborough, Mass., USA); 0.1 mM nonessential amino acids and 1 mM sodium pyruvate (Corning, Corning, N.Y., USA); and 10% fetal bovine serum (FBS; VWR Life Science Seradigm, Radnor, Pa., USA). Cells were maintained in a water-jacketed incubator at 5% CO2 and 37° C.

Figure 2B:
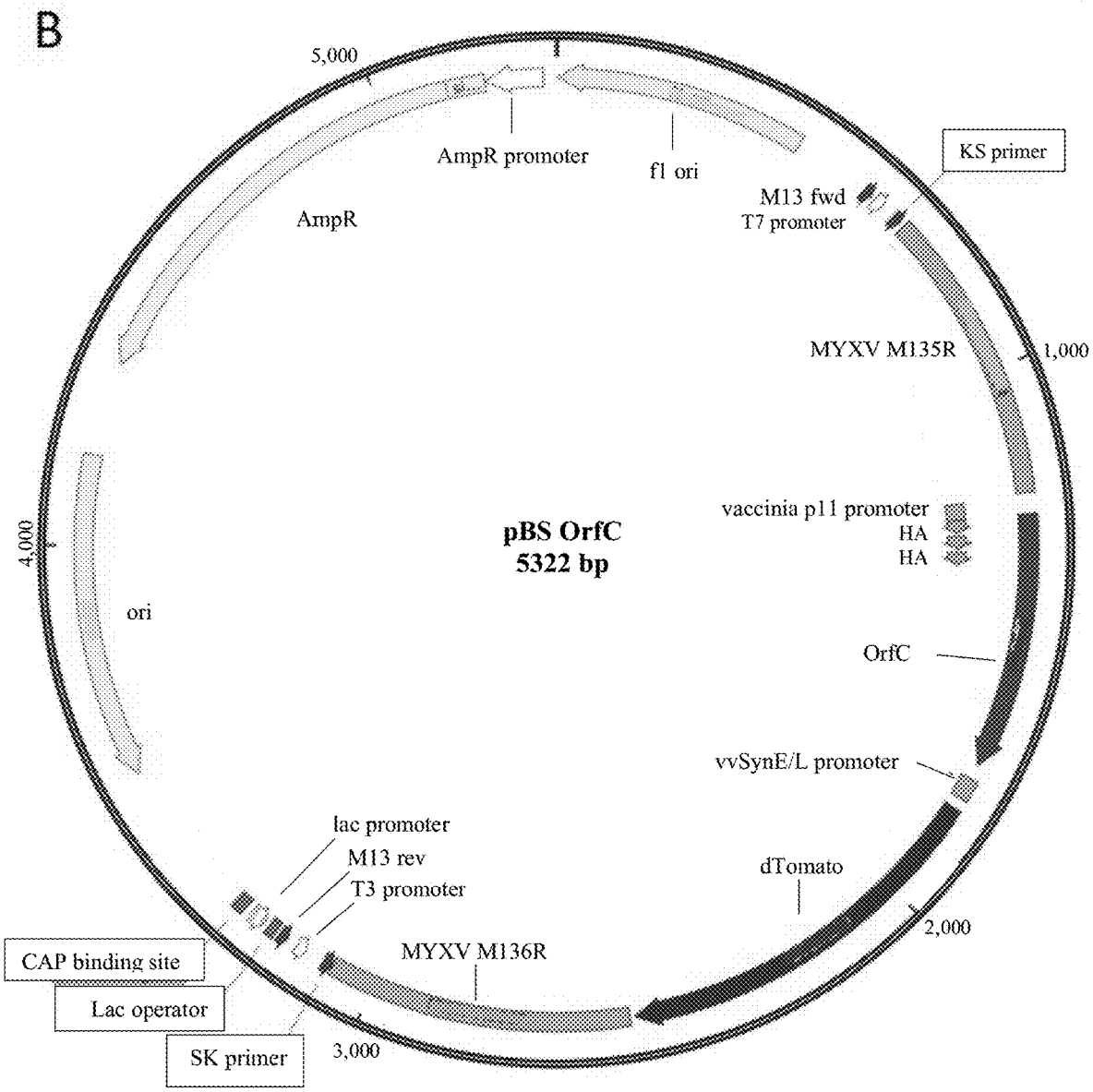
FIG. 2B is a plasmid map of a pBluscript plasmid having an HA-tagged orfC expressed by a poxvirus late gene promoter (p11) with a red fluorescent protein (tdTomato) driven by a synthetic poxvirus early/late promoter (vvSynE/L) both flanked by MYXV sequence (partial coding regions of M135R & M136R) for recombination into wild-type MYXV.

Viruses—Wild-type MYXV (Lausanne strain) and recombinant MYXV-red (originally designated vMyx-tdTr [Liu, J.; Wennier, S.; Reinhard, M.; Roy, E.; MacNeill, A.; McFadden, G. Myxoma virus expressing interleukin-15 fails to cause lethal myxomatosis in European rabbits. *J. Virol.* 2009, 83, 5933-5938.] were used in the present study. MYXVorfC was constructed by recombining a 2385 base pair (bp) PCR product into wild-type MYXV between the genetic open reading frames M135 and M136 using a pBluescript plasmid vector (FIG. 2B). Plasmid constructs were amplified by transformation into *Escherichia coli* DH5a chemically competent cells (Rapid5-a™ Hardy Diagnostics, Santa Monica, Calif., USA). Successful construction was confirmed using restriction enzyme digests and Sanger sequencing. DNA for transfection was prepared using PCR OneTaq® Mastermix (New England Biolabs, Ipswitch, Mass., USA) containing 0.5 µM of M13 forward primer (5' GTA AAA CGA CGG CCA GT 3' [SEQ ID NO. 1]), 0.5 µM of M13 reverse primer (5' CAG GAA ACA GCT ATG ACC 3' [SEQ ID NO. 2]), and 1.0 µg plasmid DNA. Amplification was performed in a thermocycler under the conditions: 94.0 for 1 min, followed by 30 cycles of 94.0 for 30 sec, 52.0 for 1 min, and 68.0 for 5 min, and a final 68.0 for 5 min step. The PCR product contained DNA sequences of: (1) the 5' fragment of MYXV M135, (2) the tandem dimer tomato red (tdTomato) under the transcriptional control of a synthetic early/late poxvirus promoter (vvSynE/L), (3) hemagglutinin (HA)-tagged WDSV orfC under the control of a late poxvirus promoter (p11), and (4) the 3' fragment of MYXV M136. Transfection of the PCR fragment was performed using a modified method described by Rice et al. 2011 [Rice, A. D.; Gray, S. A.; Li, Y.; Damon, I.; Moyer, R. W. An efficient method for generating poxvirus recombinants in the absence of selection. *Viruses* 2011, 3, 217-232.]. Briefly, RK-13 cells were infected at a multiplicity of infection (moi) of 0.01 with wild-type MYXV, transfected with 0.2 µg of PCR product DNA, and combined with Lipofectamine 2000 (Invitrogen, Carlsbad, Calif., USA) to potentiate recombination of the PCR product and viral DNA. Cells were scraped into growth media at 72 hours post-inoculation (hpi), centrifuged at 400×g for 15 min, washed in phosphate buffered saline (PBS), re-suspended in media lacking FBS, frozen and thawed three times, and sonicated. Viral lysates were serially diluted in media lacking FBS and incubated on RK-13 cells for 30 min. A solid overlay of 1 part 2× growth media and 1 part 1% agarose was placed on the infected cells. Viral foci that formed were screened for fluorescent red protein expression using a 560/40 nm bandpass excitation filter and a Leica DMI4000B inverted microscope. Fluorescent foci were isolated and expanded in RK-13 cells. The process of picking foci and growing virus was repeated nine times until only foci that expressed red fluorescent protein were observed. Viral purification was confirmed using PCR and next generation sequencing. For injection into rabbits, viruses were grown and titered in RK-13 cell cultures. Cellular debris was removed by sucrose pad purification as previously described [Condit, R. C.; Motyczka, A. Isolation and preliminary characterization of temperature-sensitive mutants of vaccinia virus. *Virology* 1981, 113, 224-241.].

Viral Growth Curves—Growth media was removed from wells of RK-13 cells when they were 80% confluent. Cells were inoculated with MYXV or MYXVorfC in media lacking FBS (moi=0.1). Cells were incubated with virus for 1 hour at 5% $CO_2$ and 37° C. Viral inoculum was removed, cells were rinsed with PBS, and growth media was added to the wells. Cells were scraped into growth media at designated time-points post-inoculation, frozen and thawed 3 times, and sonicated. Viral lysates were serially diluted in media lacking FBS and incubated on RK-13 cells for 30 minutes. A solid overlay of 1 part 2× growth media and 1 part 1% agarose was placed on the infected cells. Viral foci were counted 4 days later. The log of plaque/focus-forming units (pfu) per mL was calculated and plotted versus time.

Detection of Exogenous Protein Production by MYXVorfC—Fluorescence from tdTomato protein expression by MYXVorfC was detected using a 560/40 nm bandpass excitation filter and a Leica DMI4000B inverted microscope. Production of the HA-tagged OrfC protein was detected using a Western immunoblot. Briefly, RK-13 cells were grown in 35-mm-diameter plates to 90% confluency and inoculated with MYXVorfC (moi=0.5). Infected cells were collected into cell lysis buffer at several time points post-inoculation. Total protein concentration was determined with a standard Bradford assay and 20 µg of protein from each cell lysate was separated using SDS-PAGE (10%). The SDS-PAGE-separated proteins were transferred to a nitrocellulose membrane. Membranes were incubated in blocking buffer for 1 h. Membranes were washed then incubated with rat anti-HA IgG (Milipore Sigma, St Louis, Mo., USA) diluted 1:1000 in blocking buffer overnight at 4° C. Membranes were washed then incubated for 1 h at room temperature with a horseradish peroxidase-conjugated goat anti-rat IgG antibody (ImmunoReagents, Raleigh, N.C., USA) diluted 1:1000 in blocking buffer. A chemiluminescent western immunoblot detection kit (GE Healthcare, Marlborough, Mass., USA) was used to detect antigen-antibody complexes.

Apoptosis in Cell Culture—A RealTime-Glo Annexin V Apoptosis and Necrosis Assay kit (RealTime-Glo™ Annexin V Apoptosis and Necrosis Assay, Promega, Madison, Wis., USA) was used per the manufacturer's instructions to label cells expressing phosphatidylserine. Luminescence and fluorescence (485 nm excitation/525 nm emission) were detected using a BioTek Synergy H1 microplate reader. The ratio of the luminescent signal from cells undergoing apoptosis to the fluorescent signal from partially ruptured (necrotic) cells was calculated and graphed.

Rabbits—All animal procedures were approved by the Institutional Animal Care and Use Committee at Colorado State University (protocol #17-7708A). Twelve 8-week-old, female, New Zealand white rabbits were purchased from Western Oregon Rabbit Company (Philomath, Oreg., USA) and were acclimated for 5 days. Prior to starting the study, all rabbits were deemed healthy by physical examination including determination of heart rate and respiratory rate; auscultation of the heart and lungs; palpation of the abdomen and lymph nodes; measurement of weight and rectal temperature; evaluation of the injection site, haired skin, and mucous membranes for evidence of lesion formation; and assessment of food and water intake, grooming behavior, and mentation. An area of fur on the lateral aspect of the upper right thigh was shaved and disinfected with an accelerated hydrogen peroxide solution. Rabbits were inoculated with virus via an intradermal injection of 50 pfu of sucrose pad purified wild-type MYXV or MYXVorfC in 100 µL PBS. The area was cleaned with an accelerated hydrogen peroxide solution after the virus is administered. Rabbits were given physical examinations daily. The lesion length, width, and height at the site of inoculation were measured daily. Lesion volume was calculated as volume=length× width×height. The clinical scoring system outlined in Rice et al., JVI 2014 was used [Rice, A. D.; Adams, M. M.; Lindsey, S. F.; Swetnam, D. M.; Manning, B. R.; Smith, A. J.; Burrage, A. M.; Wallace, G.; Macneill, A. L.; Moyer, R. W. Protective Properties of Vaccinia Virus-Based Vaccines: Skin Scarification Promotes a Nonspecific Immune Response That Protects against Orthopoxvirus Disease. *J. Virol.* 2014, 88, 7753-7763.]. Animals were euthanized as soon as signs of respiratory distress were observed; if rectal temperature was less than 97 degrees Fahrenheit; if the rabbit appeared mentally dull with poor response to noise or light; if the rabbit stopped grooming, eating, or drinking; or at Day 21 post-inoculation.

Sample Collection—Prior to euthanasia, rabbits were anesthetized with a freshly-mixed combination of 50 mg/kg ketamine and 10 mg/kg xylazine by intramuscular injection into the proximal and lateral aspect of the left thigh. Fully anesthetized rabbits (unresponsive to noxious stimulation, such as pinching the toes with forceps) were administered an overdose of intracardiac pentobarbital (120 mg/kg) to ensure they were deceased. After euthanasia, a necropsy was performed to collect skin lesions and all internal organs. Two sections of each tissue were collected; one was flash frozen in liquid nitrogen for isolation of virus and detection of viral DNA and one was preserved in 10% buffered formalin for histopathology.

Detection of Virus in Tissues—Flash frozen tissue sections were weighed and homogenized. Samples were serially diluted in media without FBS, sonicated, and inoculated onto RK-13 cells for 30 minutes. A solid overlay of 1 part 2× growth media and 1 part 1% agarose was placed on the infected cells. Viral foci were counted 4-6 days later. Pfu per mg of tissue calculated. Additionally, DNA was isolated from sample homogenates using a tissue DNA isolation kit (DNeasy Blood and Tissue Kit, QIAGEN, Hilden, Germany). 54, of DNA was used in PCR reactions with two primer sets. A set of primers that detect a multigenic region of the MYXV genome that includes M032R, M033R, M034L (DNA polymerase), and M035R were used to detect MYXV in tissues (Forward 5' CAC CCT CTT TAG TAA AGT ATA CAC C 3' [SEQ ID NO. 3], Reverse 5' GAA ATG TTG TCG GAC GGG 3' [SEQ ID NO. 4]). An 800 bp product is detected for both MYXV and MYXVorfC with these primers. A second set of primers were also used (Forward 5' ACA TAC GAC ATC GGA CAG CA 3' [SEQ ID NO. 5], Reverse 5' CGT CGA TCG CTG TGT AAG AA 3' [SEQ ID NO. 6]) that covered the region of the gene insert (M135-M136); a 320 bp product is expected for wild-type MYXV and a 1547 bp product is expected for MYXVorfC. Amplification was performed in a thermocycler under the conditions: 94.0 for 1 min, followed by 30 cycles of 94.0 for 30 sec, 55.0 for 1 min, 72.0 for 2 min and a final 72° C. for 10 min elongation step.

Histopathology—Formalin-fixed tissue was paraffin embedded, sectioned, and stained with Hematoxylin and Eosin (H&E) for histologic evaluation. The extent of inflammation, necrosis, and edema observed in skin lesions histologically was graded as previously described [Doty, R. A.; McFadden, G.; Roy, E. J.; MacNeill, A. L. Histological evaluation of intratumoral myxoma virus treatment in an immunocompetent mouse model of melanoma. *Oncolytic Virotherapy* 2013, 2, 1-17.]. Similarly, additional sections were used to detect apoptosis using a TUNEL (TdT-mediated dUTP Nick End Labeling) assay (Click-iT™ TUNEL, Life Technologies, Carlsbad, Calif., USA) and the extent of apoptosis was graded.

Statistical Analysis—Median survival time was calculated using Kaplan-Meier survival curves. The apoptosis to necrosis ratio in RK-13 cells; clinical scores, respiratory rate, heart rate, body temperature, and lesion volume in rabbits; virus titers in tissues; and the extent of inflammation, necrosis, edema, and apoptosis in histologic sections were compared using t-tests. All data were analyzed using GraphPad Prism version 8.1.0 software (San Diego, Calif., USA).

Example 2—Validation of MYXVorfC Construction

Figure 3A:
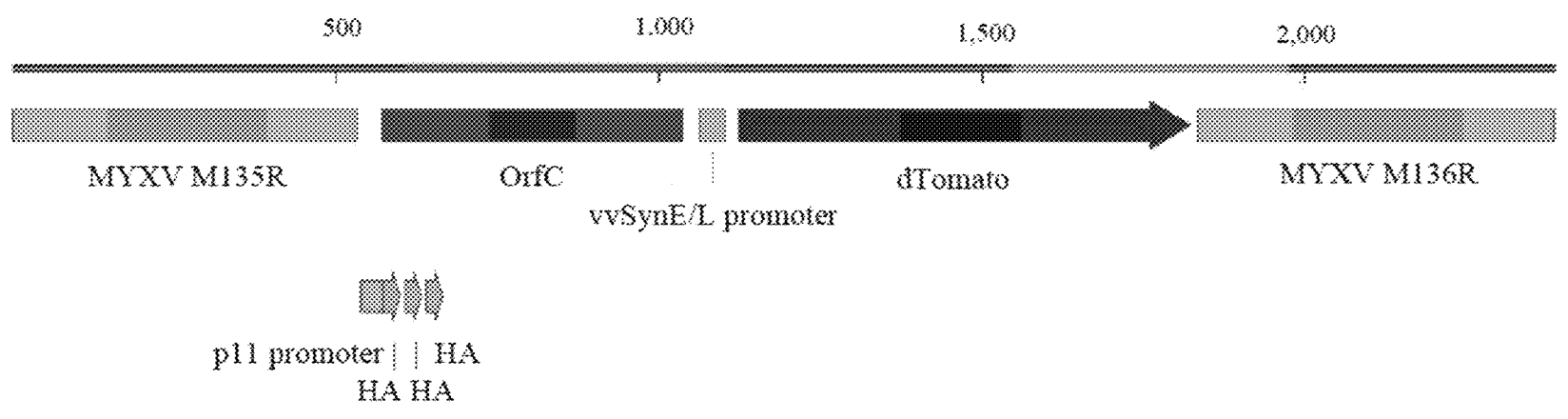
Figure 3B:
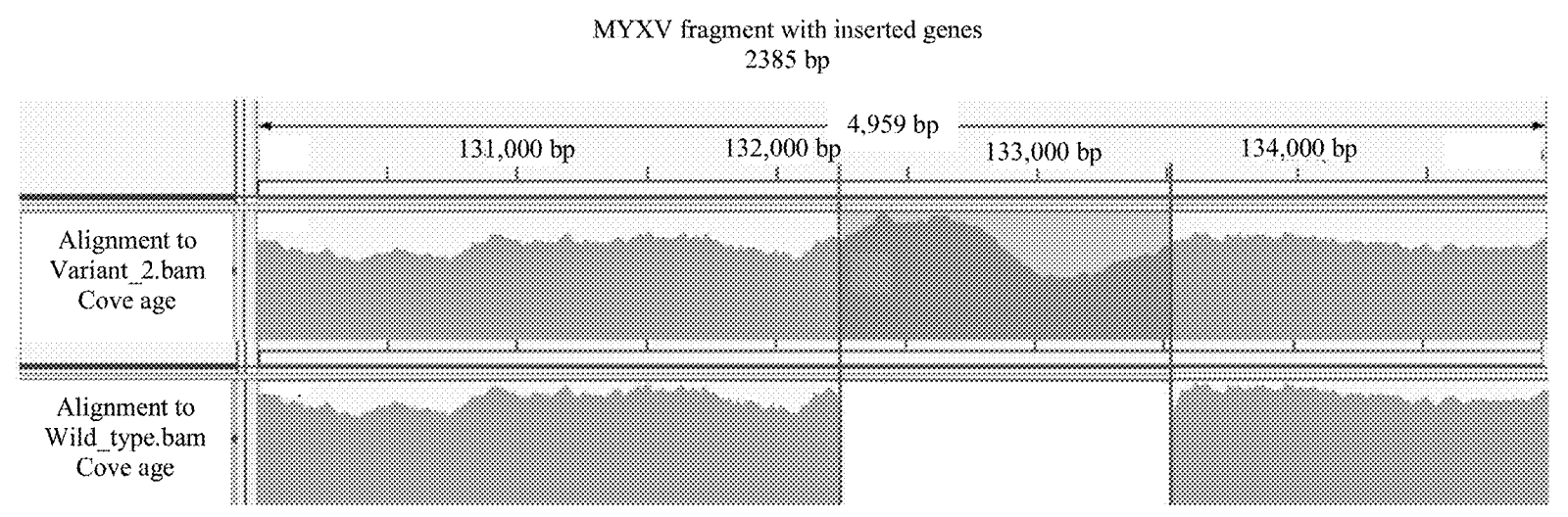
Figure 4:
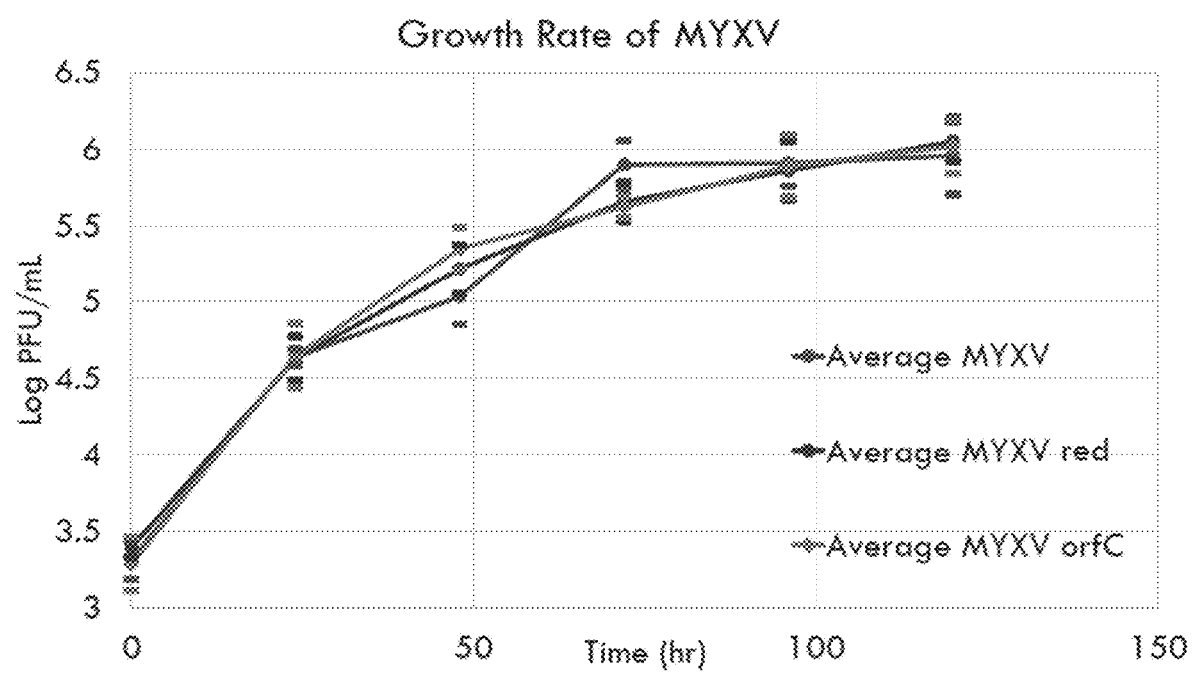
Figure 5:
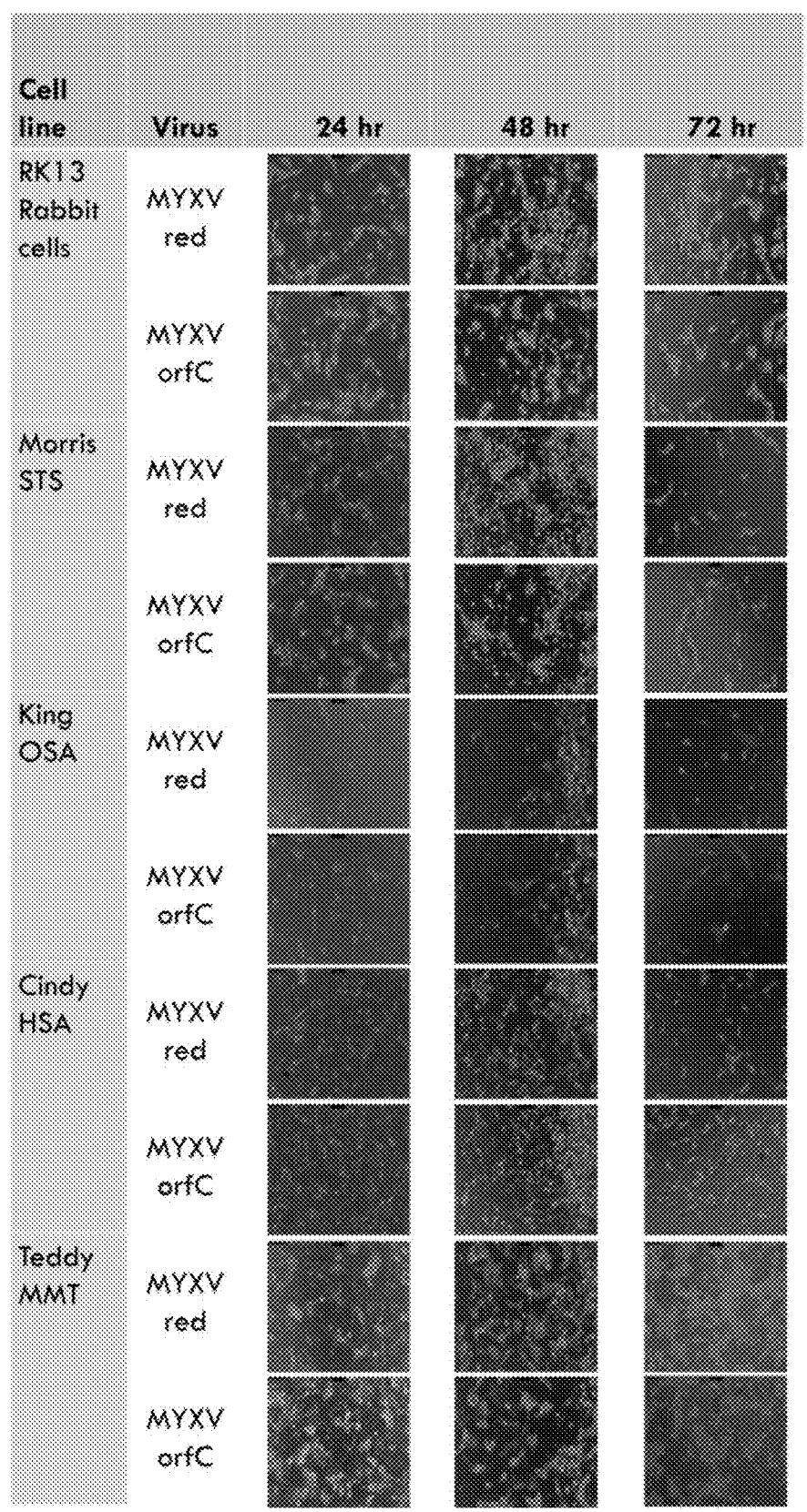
FIG. 5 is a set of images showing complete microscopic analysis of MYXV red and MYXV orfC infection in rabbit kidney epithelial cells (RK13) and five types of canine cancer cells at three time points after infection [multiplicity of infection (moi)=1 infectious virus particle per cell]. The figure(s) shows microscopic images of cells 48 hours after inoculation without virus (Mock) or with a recombinant virus at a multiplicity of infection of 1 (MYXV Red or MYXV OrfC).
Figure 7:
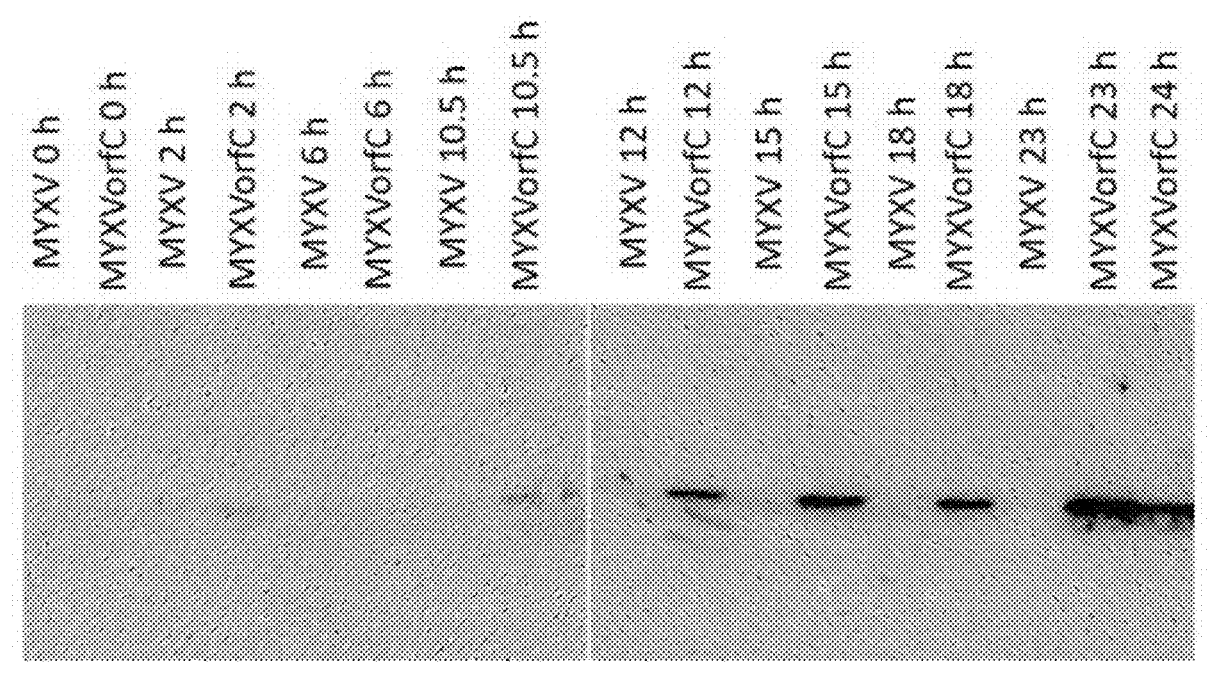
Figure 8:
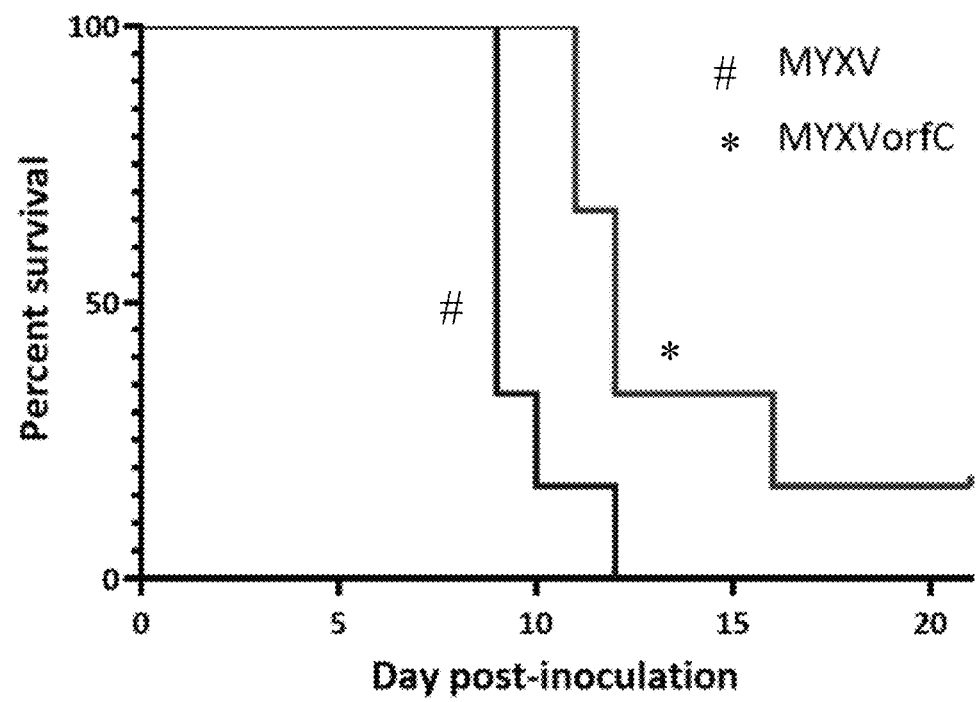
FIG. 8 is a graph showing the median survival time of rabbits infected with 50 pfu MYXV was significantly shorter than that of rabbits infected with 50 pfu MYXVorfC (p-value=0.05).

A diagram of the PCR product introduced between genes M135 and M136 to create the recombinant MYXVorfC virus is shown in FIG. 3A. Restriction enzyme digestions of MYXVorfC indicated the predicted DNA fragment lengths. MYXVorfC sequence analysis indicated that no unexpected genetic changes were caused during recombination of the PCR fragment into wild-type MYXV (FIG. 3B). Growth curve kinetics of wild-type MYXV and MYXVorfC in RK-13 cells were statistically indistinguishable (FIG. 4) indicating that insertion of the PCR product did not negatively affect MYXVorfC replication in permissive RK-13 cells. Next, protein expression of orfC and tdTomato by MYXVorfC was assessed. Red fluorescence was detected in RK-13 cell cultures and canine cancer cells inoculated with MYXVorfC (FIG. 5—see lighter grey regions). The number of cells expressing tdTomato was similar when MYXV-red and MYXVorfC infections were compared in each cell type (FIG. 7). OrfC protein expression was detected by 12 hpi using western blot analysis (FIG. 8). Together, these data indicate that tdTomato and orfC were successfully inserted into wild-type MYXV to create a recombinant MYXVorfC that expresses detectable amounts of tdTomato and orfC proteins.

Example 3—Apoptotic Upregulation by Myxoma Virus Expressing Walleye Dermal Sarcoma Virus orfC MYXV orfC virus is able to infect canine cancer cells & induce apoptosis. Infection with MYXV orfC is possible in different types of cancer cells as shown below. MYXV orfC was generated as described above in Example 1 using the plasmid as shown in FIG. 2B starting from the DNA fragment shown in FIG. 3A.

Figure 6:
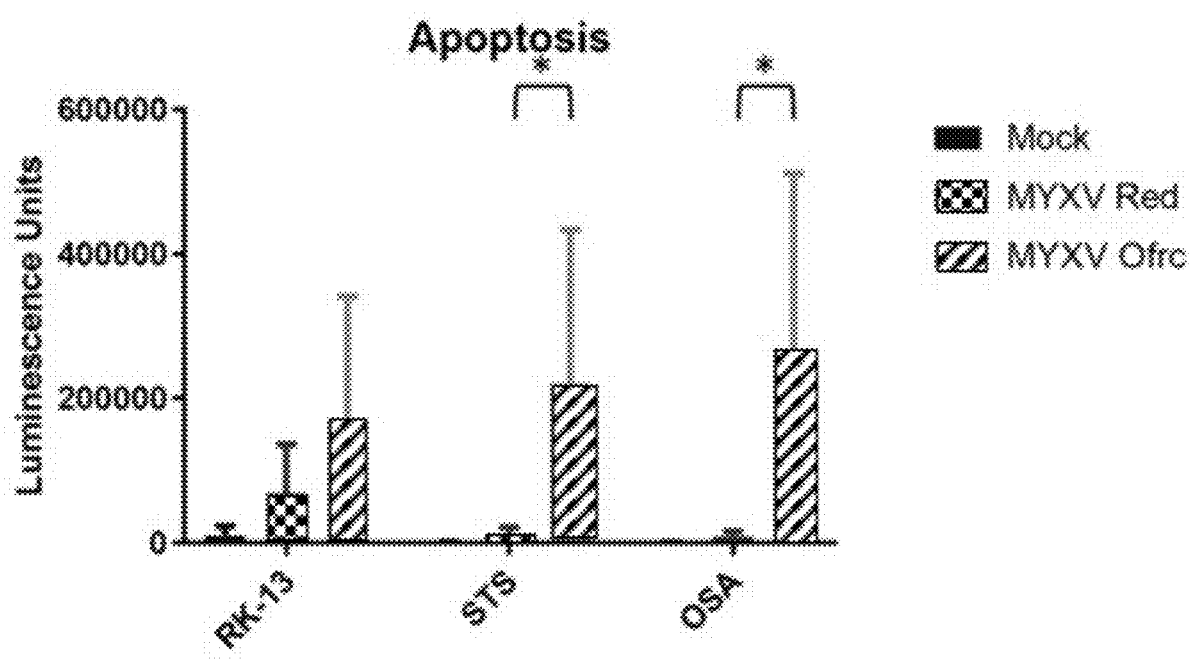
FIG. 6 is a graph showing that apoptosis is evident in MYXV orfC-infected cells at 48 h post-infection (moi=1). P-values were <0.05 in canine cancer cells. The figure shows the detection of Annexin V-labeled cells using a RealTime-Glo Annexin V apoptosis and necrosis assay (Promega). Rabbit kidney epithelial cells (RK-13), canine soft tissue sarcoma cells (STS), and canine osteosarcoma cells (OSA) were collected 48 hours after inoculation without virus (mock) or with a recombinant virus at a multiplicity of infection of 1 (MYXV Red or MYXV OrfC). Apoptosis (indicated by luminescence units) was significantly higher in MYXV OrfC-infected canine cells as compared to MYXV Re-infected canine cells (*).

FIG. 3B shows the alignment of purified recombinant MYXVorfC DNA compared to MYXV (AF170726.2) using next generation sequencing. The expected PCR insert was successfully recombined into MYXV to create MYXVorfC (see the region between 132,000 bp and 134,000 bp in FIG. 3B). Wild-type MYXV sequence was not detected in the purified MYXVorfC virus sample. No significant differences were observed in the growth of wild-type MYXV, MYXV-red, or MYXVorfC (FIG. 4). In other words, MYXV replication is not altered by tomato red & orfC gene inserts. Expression of the orfC protein by MYXV orfC was detected in cells 12 h post-inoculation (FIG. 7). Expression of tdTomato was observed in RK-13 cells and canine cancer cells infected with MYXV red and MYXV orfC (FIG. 5). Apoptosis is significantly greater in MYXVorfC than in MYXV or MYXV-red at 48 hours post-infection (FIG. 6).

The present invention demonstrates the successful recombination of the orfC gene of WDSV into MYXV, with the correct sequence detected within the recombinant virus. It further demonstrates orfC protein production at a late time point, with no change in growth rate of MYXV orfC in cells, such as RK13 cells. Moreover, the successful infection of canine cancer cells with MYXV orfC is demonstrated, with cytopathic effects observed microscopically and tomato red protein expression observed using fluorescent microscopy and microplate readers. MYXV orfC is demonstrated to induce apoptosis in MYXV orfC-infected cancer cells. In summary, MYXV orfC is as capable of infecting RK13 & canine cancer cells as wild-type MYXV and MYXV red. Additionally, MYXV orfC causes apoptosis more effectively than MYXV red.

Example 4—Apoptosis is Induced by MYXVorfC

The purpose of using MYXV to express the orfC protein was to enhance apoptosis in infected cancer cells. Apoptosis was greatly increased in RK-13 cells infected with MYXVorfC as compared to MYXV-red infected or mock-infected cells (FIG. 7).

Example 5—MYXVorfC is Attenuated in Rabbits

Figure 9:
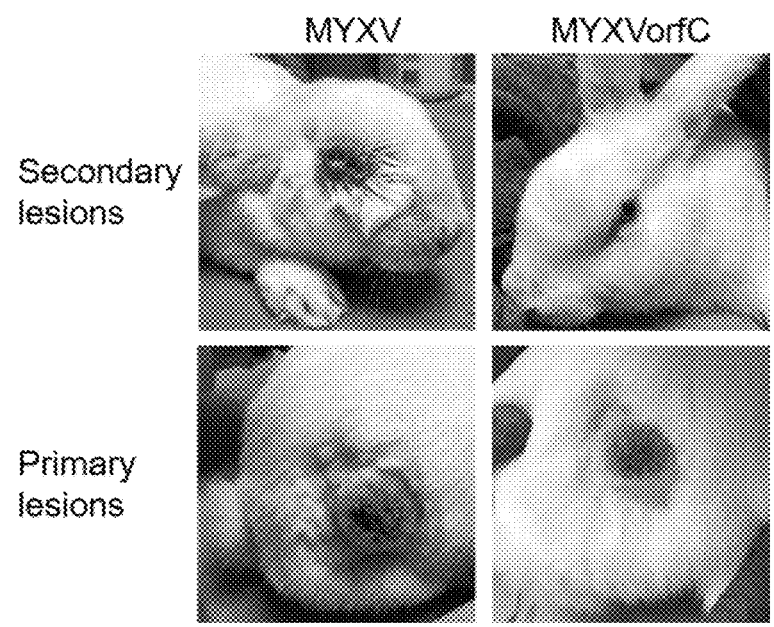
FIG. 9 is a set of representative images of gross skin lesions 9 days after intradermal inoculation of 50 pfu MYXV or MYXVorfC on the right thigh.
Figure 10:
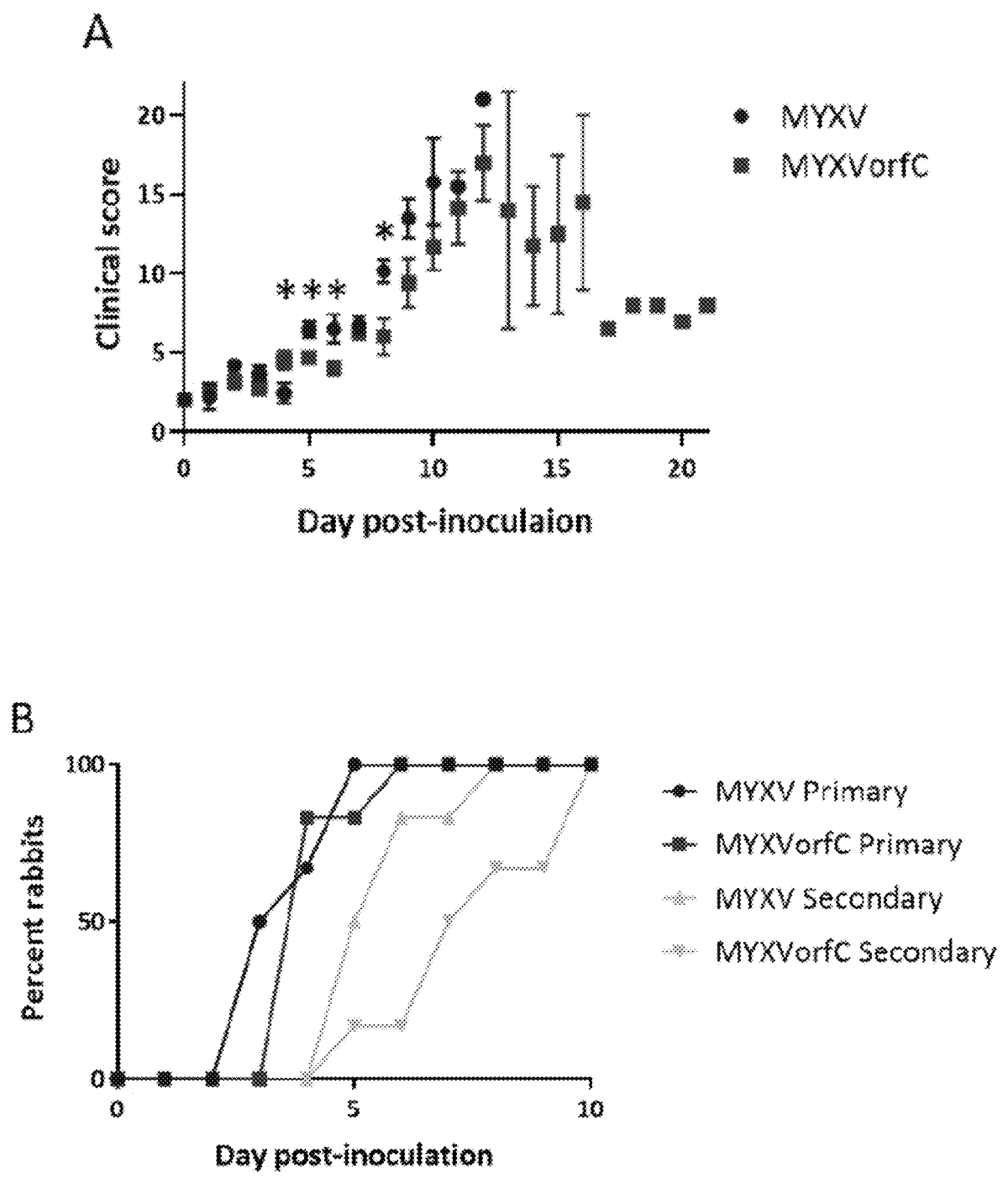
Figure 11:
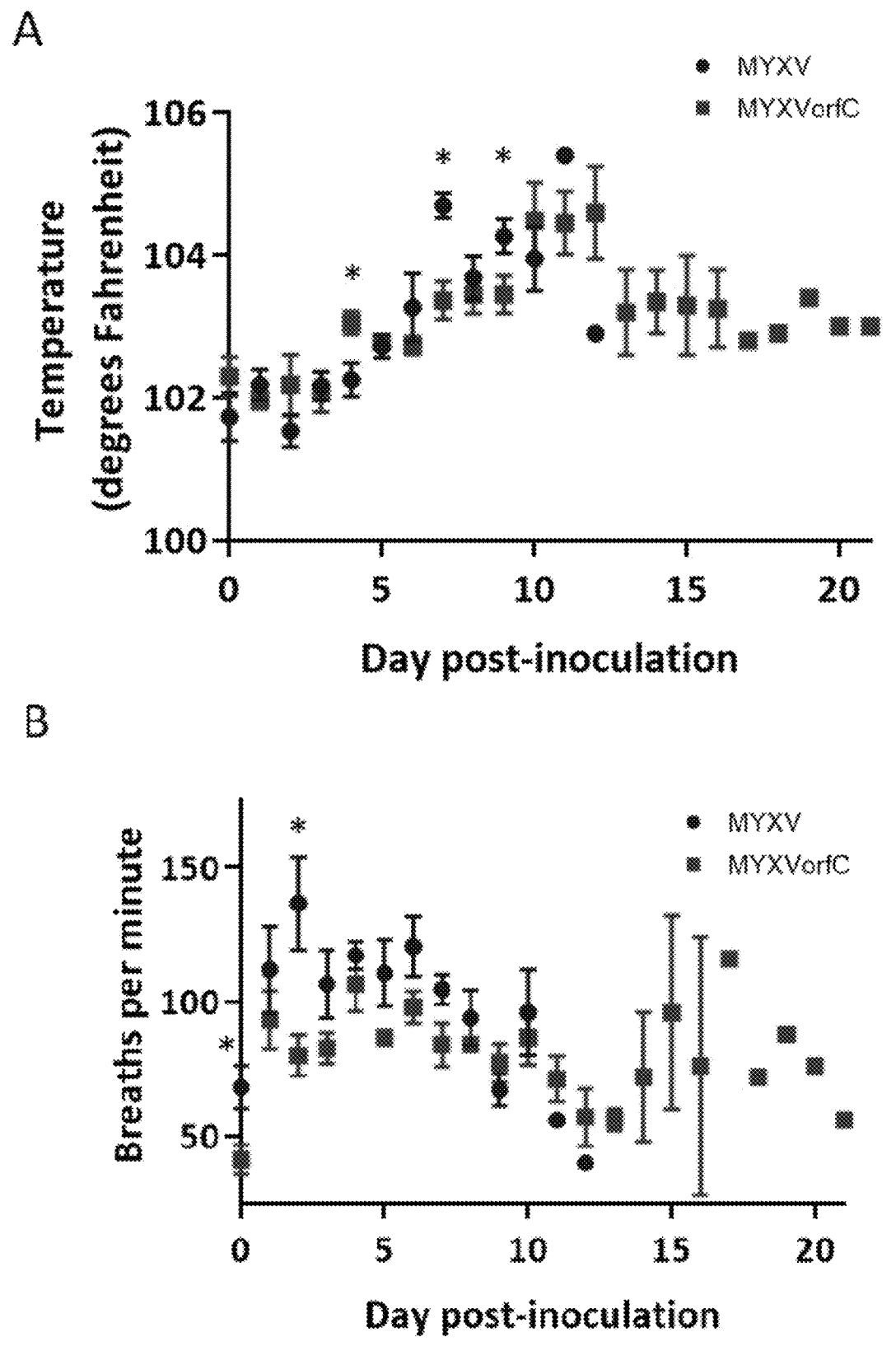
Figure 12:
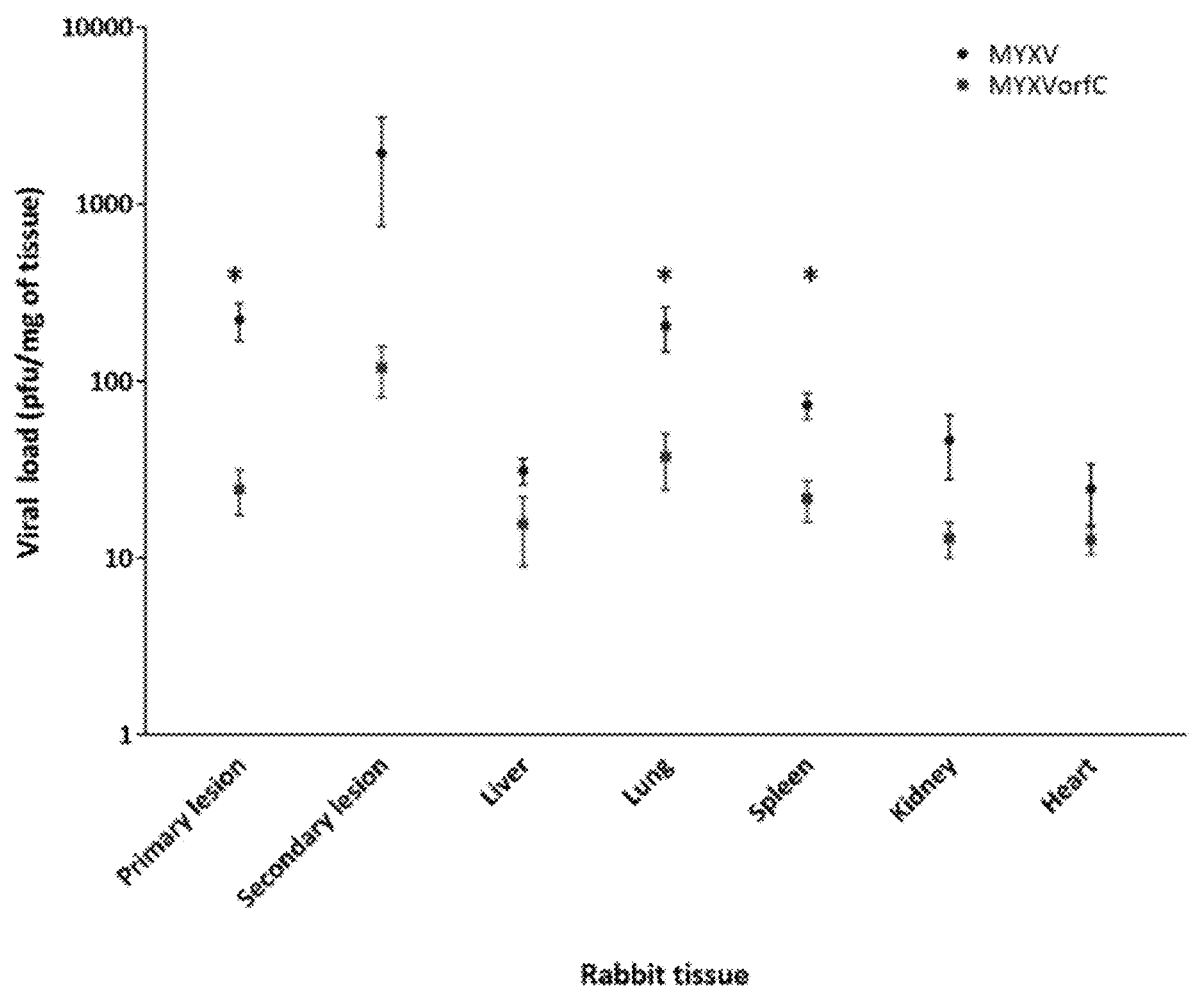

All New Zealand white rabbits infected with 50 pfu wild-type MYXV needed to be euthanized due to respiratory distress. One of six rabbits infected with 50 pfu of MYXVorfC survived. The median survival time of rabbits inoculated with MYXVorfC was significantly greater than that of rabbits inoculated with MYXV (FIG. 8). The median survival times for MYXV- and MYXVorfC-infected rabbits were 9 and 12 days post-inoculation (dpi), respectively. Development of clinical signs of disease (including respiratory distress and dissemination of virus to form edematous, ulcerative skin lesions) was slightly delayed in rabbits infected with MYXVorfC (FIG. 9). Slightly, but significantly, lower clinical scores were observed in MYXVorfC rabbits on Days 5, 6, and 8 after virus injection (FIG. 10A). These differences were attributed to the delay in development of secondary lesions on mucus membranes and ear pinnae in rabbits infected with MYXVorfC (FIG. 10B) and detection of fever (body temperature>104° C., FIG. 11A). Small differences in mean respiratory rate (FIG. 11B), heart rate (FIG. 11C) were found on certain dpi, but no definitive trends were seen over time. No significant differences in lesion volume were calculated, but the average volume of the primary lesion of rabbits infected with MYXVorfC decreased in animals that survived beyond Day 12 pi (FIG. 11D). These data indicate that MYXVorfC is less pathogenic than wild-type MYXV Example 6—MYXVorfC Tissue Tropism is not Altered Dissemination of wild-type MYXV and MYXVorfC during infection of rabbits appeared similar. Viral DNA was detected in skin, lungs, heart, spleen, liver, and kidney in all MYXV-infected rabbits and most MYXVorfC-infected rabbits (Table 1). Viral titers (indicating the presence of infectious virions) were significantly lower in the primary lesions, lungs, and spleen of the MYXVorfC-infected rabbits when compared to MYXV-infected rabbits (FIG. 12). Viral DNA could be detected in tissues with titers as low as 2.5 pfu/mg. All tissues with titers>35 pfu/mg were positive for viral DNA by PCR using both primer sets.

TABLE 1

Detection of MYXV or MYXVorfC by PCR in rabbit tissues collected at the time of euthanasia from rabbits inoculated with 50 pfu MYXV or MYXVorfC.

| Virus | Tissue | Viral DNA Targets of Primers | |
|---|---|---|---|
| | | Multigene | M135-M136 |
| MYXV | Primary lesion | 6/6 (100%) | 6/6 (100%) |
| | Secondary lesion | 6/6 (100%) | 6/6 (100%) |
| | Heart | 6/6 (100%) | 6/6 (100%) |
| | Kidney | 6/6 (100%) | 6/6 (100%) |
| | Liver | 6/6 (100%) | 6/6 (100%) |
| | Lung | 6/6 (100%) | 6/6 (100%) |
| | Spleen | 6/6 (100%) | 6/6 (100%) |
| MYXVorfC | Primary lesion | 6/6 (100%) | 6/6 (100%) |
| | Secondary lesion | 6/6 (100%) | 6/6 (100%) |
| | Heart | 3/6 (50%) | 3/6 (50%) |
| | Kidney | 5/6 (83%) | 5/6 (83%) |
| | Liver | 6/6 (100%) | 5/6 (83%) |
| | Lung | 6/6 (100%) | 5/6 (83%) |
| | Spleen | 4/6 (67%) | 3/6 (50%) |

Example 7—MYXV and MYXVorfC Induce Similar Histologic Lesions

Figure 13:
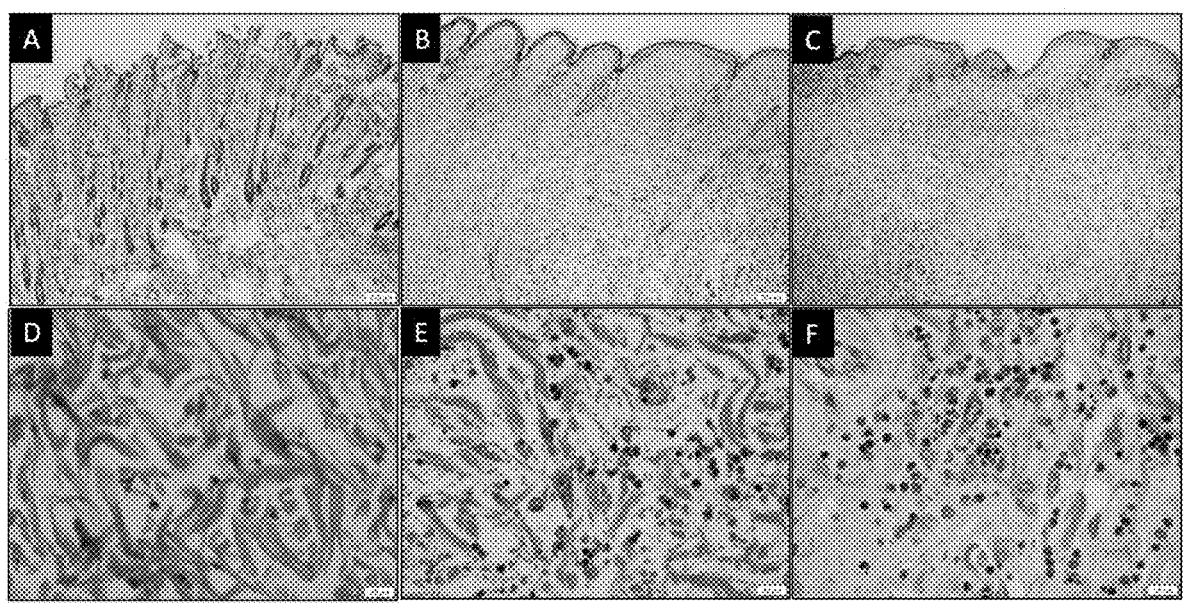
FIG. 13 is a set of six photomicrographs of skin from the lateral thigh of rabbits injected with (A & D) saline, (B & E) 50 pfu MYXV, or (C & F) 50 pfu MYXVorfC. Samples were collected at the time of euthanasia, processed, and stained with H&E (A, B & C magnification 10× objective; D, E & F magnification 40× objective).

No overt histologic abnormalities were observed in heart or kidney sections. Viral pneumonia was observed in lung tissue from all rabbits with mild to moderate edema and diffuse suppurative inflammation. Sloughing of bronchial epithelial cells into the bronchial lumen was noted. Mild hyperplasia of perivascular lymphoid tissue of the lungs was observed in both MYXV- and MYXVorfC-infected rabbits. Evidence of disease in the liver was more variable. Mild diffuse lymphocytic inflammation was observed in the livers of 67% (4/6) MYXV-infected rabbits and 33% (2/6) MYXVorfC-infected rabbits. Mild diffuse mixed inflammation (including neutrophils, histiocytes, lymphocytes, and plasma cells) was observed in the liver of 50% (3/6) MYXVorfC-infected rabbits. No inflammation was observed in the liver of the remaining 33% (2/6) MYXV-infected and 17% (1/6) MYXVorfC-infected rabbits. Tissue sections from primary and secondary skin lesions of all rabbits had the classic appearance of myxomatosus in European rabbits. A large focus of full-thickness dermal necrosis was associated with several large reactive fibroblasts and myxedema (FIG. 13). Fibroblasts and epithelial cells sometimes contained a large basophilic cytoplasmic viral inclusion. Marked suppurative inflammation was present within the necrotic lesion and moderate mononuclear inflammation surrounded the damaged tissue. The average number of TUNEL positive cells in ten 40× objective microscopic fields in sections of primary skin lesions was not significantly different in MYXV- and MYXVorfC-infected rabbits (FIG. 14). The secondary lesion from one MYXVorfC-infected rabbit was beginning to heal with extension of the epidermis under a layer of fibrin and cellular debris.

Example 8—MYXVorfC Stimulates Follicular Hyperplasia in Lymphoid Tissues

Figure 15:
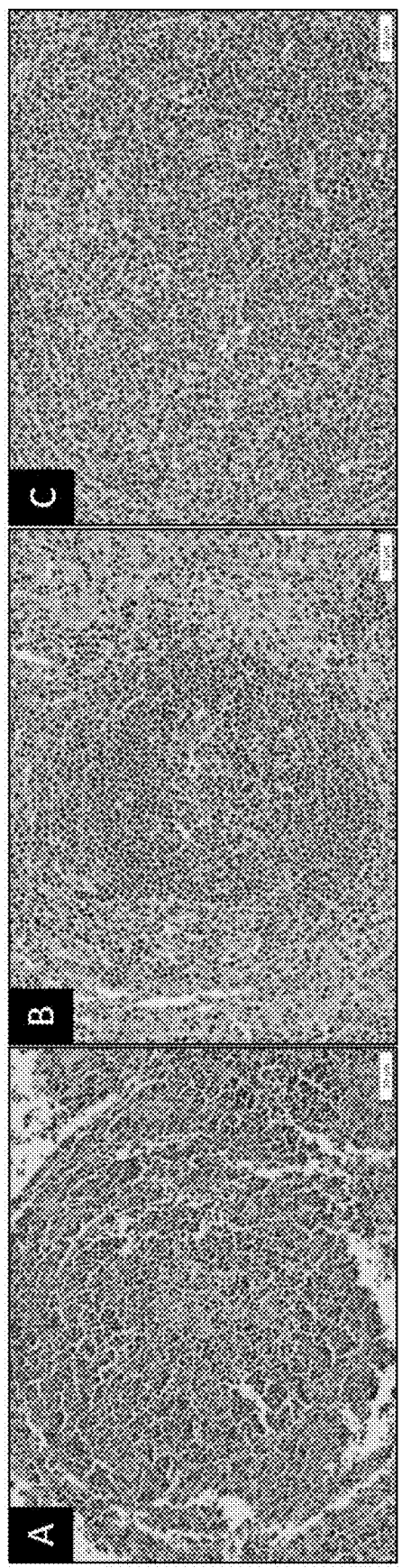
FIG. 15 is a set of three representative photomicrographs of splenic lymphoid follicles from rabbits injected with (A) saline, (B) 50 pfu MYXV, or (C) 50 pfu MYXVorfC. Samples were collected at the time of euthanasia. Marked follicular hyperplasia was noted in rabbits infected with MYXVorfC (H&E, magnification 20× objective).

Spleen and lymph nodes from uninfected rabbits and rabbits infected with MYXV had minimal lymphoid reactivity (FIGS. 15A & 15B). In contrast, MYXVorfC-infected rabbits developed lymphoid hyperplasia (FIG. 15C) suggestive of a more activated adaptive systemic immune response to the virus.

Development of safe, effective OVs could revolutionize cancer treatment, particularly for neoplasms that are refractory to currently available therapies. MYXV is nonpathogenic in humans [Jackson, E. W.; Dorn, C. R.; Saito, J. K.; McKercher, D. G. Absence of serological evidence of myxoma virus infection in humans exposed during an outbreak of myxomatosis. *Nature* 1966, 211, 313-314.] and shows potential as a safe OV [MacNeill, A. L.; Weishaar, K. M.; Séguin, B.; Powers, B. E. Safety of an oncolytic myxoma virus in dogs with soft tissue sarcoma. *Viruses* 2018, 10, 10-23; Kinn, V. G.; Hilgenberg, V. A.; MacNeill, A. L. Myxoma virus therapy for human embryonal rhabdomyosarcoma in a nude mouse model. *Oncolytic Virotherapy* 2016, 5, 59-71.]. However, the effectiveness of MYXV is limited. OVs that induce apoptosis of tumor cells quickly can expose the immune response to tumor antigens more rapidly and negate limitations of rapid removal of MYXV, which may be due to the anti-viral response induced by healthy cells within the tumor microenvironment. Accordingly, a pro-apoptotic, recombinant MYXV, MYXVorfC was developed and is taught herein.

MYXVorfC contains an HA-tagged orfC gene isolated from WDSV. WDSV orfC is thought to promote seasonal tumor regression in fish infected with WDSV by inducing cytochrome C release from mitochondria [Nudson, W. A.; Rovnak, J.; Buechner, M.; Quackenbush, S. L. Walleye dermal sarcoma virus Orf C is targeted to the mitochondria. *J. Gen. Virol.* 2003, 84, 375-381.]. Expression of orfC by MYXVorfC was placed under the control of a late poxvirus promoter element (vaccinia p11) with the expectation that complete replication of MYXVorfC and production of infectious virions would occur before significant apoptosis was induced in infected cells. Additionally, MYXVorfC was engineered to encode the reporter element tdTomato under the control of an early/late poxvirus promoter (vvSynE/L) to enable screening for, and plaque purification of, recombinant virus. The sequencing data indicated that the HA-tagged orfC gene and the reporter element tdTomato successfully recombined into wild-type MYXV. The virus growth curve in RK-13 cells was not altered by recombination of tdTomato or HA-orfC into MYXV. Protein expression of tdTomato was observed as early as 8 hpi and HA-tagged orfC was detected by 12 hpi. Importantly, MYXVorfC significantly increased in apoptosis in cell culture as compared to wild-type MYXV.

Next, New Zealand white rabbits were infected with MYXVorfC to ensure that the pathogenicity of the recombinant virus was not more severe than wild-type MYXV. During wild-type MYXV infection, virus replicates to high titers at the primary site of virus inoculation. Within 2 to 4 dpi, viremia occurs allowing for systemic dissemination of infectious viral particles. MYXV localizes to the skin and mucous membranes by 5 dpi, replicates to high titers, and causes secondary myxomatous lesions, fever, and viral pneumonia. This leads to severe obstruction of the respiratory tract, respiratory arrest, and death between 8 and 12 dpi. [MacNeill, A. L.; Turner, P. C.; Moyer, R. W. Mutation of the Myxoma virus SERP2P1-site to prevent proteinase inhibition causes apoptosis in cultured RK-13 cells and attenuates disease in rabbits, but mutation to alter specificity causes apoptosis without reducing virulence. *Virology* 2006, 356, 12-22.]. In comparison, rabbits infected with MYXVorfC had a significantly longer median survival time. Five animals required euthanasia between 11 and 16 dpi, but one animal recovered from MYXVorfC infection. Differences in overall clinical scores were minimal and mostly due to a short delay in the development of secondary lesions and fever in rabbits infected with MYXVorfC.

Although MYXVorfC infection was attenuated, the dissemination of MYXVorfC was similar to MYXV. Virus DNA and infectious virions were detected for both viruses in all organs tested. However, significantly lower MYXVorfC titers were recovered from the primary skin lesion at the site of inoculation, the lung tissue, and the spleen. This could reflect a mild reduction of MYXVorfC replication in rabbit tissues or increased clearance of the virus by the immune response. MYXVorfC rabbits had clear evidence of lymphoid hyperplasia, which was lacking in MYXV-infected rabbits. This suggests that rabbits mount a more effective immune response against MYXVorfC.

MYXVorfC was engineered to increase apoptosis during infection. This was confirmed using RK-13 cells in tissue culture. In rabbits, the average number of TUNEL positive cells in MYXV-infected primary lesions (26.7±11.7/hpf) was lower than that of MYXVorfC-infected lesions (37.2±7.1/hpf). Although this difference was not statistically significant, a slight increase in TUNEL positive cells was consistently observed in MYXVorfC-infected tissue. MYXV-induced apoptosis should prove enhanced in cancerous cells. Since MYXVorfC is pro-apoptotic in cell culture and attenuated in rabbits, MYXVorfC treatment should prove more effective than MYXV at eliminating cancer.

Glossary of Claim Terms

The term "administration" and variants thereof (e.g., "administering" a compound, "administering" a recombinant myxoma virus) in reference to a compound of the invention means introducing the compound into the system of the subject in need of treatment. When a compound of the invention is provided in combination with one or more other active agents (e.g., a cytotoxic agent, etc.), "administration" and its variants are each understood to include concurrent and sequential introduction of the compound and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound (e.g. an oncolytic virus) or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation or metastasis of the tumor. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

The present invention relates to oncolytic viral therapy; more specifically to treat, prevent or inhibit disease characterized by aberrant cellular proliferation, particularly cancer.

An oncolytic virus is a virus which preferably lyses cancer cells, while having little effect on non-cancer cells. Oncolytic virotherapy constitutes an advantageous therapeutic approach for completing the arsenal of available anti-cancer therapies.

The myxomatosis virus (MYXV), also called Myxoma virus, belongs to the genus Leporipoxvirus in the Poxviridae family. It is the agent responsible for myxomatosis, a major infectious disease in European rabbits and an endemic disease in Europe. This virus exhibits a narrow host range and is not pathogenic for humans. It represents a particularly advantageous virus for use in oncolytic viral therapy.

The myxoma virus may be any myxoma virus that belongs to the Leporipoxvirus species of poxviruses and that is replication-competent. The myxoma virus may be a wild-type strain of myxoma virus or it may be a genetically modified/recombinant strain of Myxoma virus.

The virus may be administered to the patient using standard methods of administration. In one embodiment, the virus is administered systemically. In another embodiment, the virus is administered by injection at the disease site. In a particular embodiment, the disease state is a solid tumor and the virus is administered by injection at the tumor site. In various embodiments, the virus may be administered orally or parenterally, or by any standard method known in the art.

When administered to a patient, an effective amount of the virus is the amount required, at the dosages and for sufficient time period, to alleviate, improve, mitigate, ameliorate, stabilize, prevent the spread of, slow or delay the progression of or cure the disease. For example, it may be an amount sufficient to achieve the effect of reducing the number or destroying cancerous cells or neoplastic cells or reducing the number of or destroying cells chronically infected with a virus, or inhibiting the growth and/or proliferation of such cells.

The effective amount to be administered to a patient can vary depending on many factors such as the pharmacodynamic properties of the virus, the mode of administration, the age, health and weight of the patient, the nature and extent of the disease state, the frequency of the treatment and the type of concurrent treatment, if any, and the virulence and titer of the virus.

One of skill in the art can determine the appropriate amount based on the above factors. The virus may be administered initially in a suitable amount that may be adjusted as required, depending on the clinical response of the patient. The effective amount of virus can be determined empirically and depend on the maximal amount of the virus that can be administered safely, and the minimal amount of the virus that produces the desired result.

To produce the same clinical effect when administering the virus systemically as that achieved through injection of the virus at the disease site, administration of significantly higher amounts of virus may be required. However, the appropriate dose level should be the minimum amount that would achieve the desired result.

The concentration of virus to be administered will vary depending on the virulence of the particular strain of Myxoma that is to be administered and on the nature of the cells that are being targeted. In one embodiment, a dose of less than about $10^9$ plaque forming units ("pfu") is administered to a human patient. In various embodiments, between about $10^2$ to about $10^9$ pfu, between about $10^2$ to about $10^7$ pfu, between about $10^3$ to about $10^6$ pfu, or between about $10^4$ to about $10^5$ pfu may be administered in a single dose.

Effective amounts of virus can be given repeatedly, depending upon the effect of the initial treatment regimen. Administrations are typically given periodically, while monitoring any response. It will be recognized by a skilled person that lower or higher dosages than those indicated above may be given, according to the administration schedules and routes selected.

The virus may be administered alone or in combination with other therapies, including chemotherapy, radiation therapy or other anti-viral therapies. For example, the virus may be administered either prior to or following surgical removal of a primary tumor or prior to, concurrently with or following treatment such as administration of radiotherapy or conventional chemotherapeutic drugs. In one embodiment, the virus can be administered in combination with, or in a sequential fashion with, other oncolytic viruses, which may demonstrate specificity for varying tumor cell types.

To aid in administration, the virus may be formulated as an ingredient in a pharmaceutical composition. Therefore, in a further embodiment, there is provided a pharmaceutical composition comprising Myxoma virus and a pharmaceutically acceptable diluent. compositions may routinely contain pharmaceutically acceptable concentrations of salt, buffering agents, preservatives and various compatible carriers. For all forms of delivery, the recombinant virus may be formulated in a physiological salt solution.

A "subject in need of treatment" is a mammal with cancer that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "a cell" as used herein includes a single cell as well as a plurality or population of cells. Administering an agent to a cell includes both in vitro and in vivo administrations.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "pretreating", or "pretreatment", is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment. It is envisioned that pretreatment with a chemotherapeutic agent can be performed 1 hr., 2 hrs., 4 hrs., 8 hrs., 1 day, 2 days, 4 days, 1 week, 2 weeks, or 1 month prior to treatment.

In accordance with another aspect of the invention, therapeutic agents of the present invention, such as agents that are effective to increase the susceptibility of a tumor or cancer cell to oncolytic viral infection in a host, may be provided in containers or kits having labels that provide instructions for use of agents of the invention, such as instructions for use in treating cancers Kits for practicing the methods of the invention are further provided. By "kit" is intended any manufacture (e.g., a package or a container) comprising at least one reagent, e.g., a pH buffer of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

In an advantageous embodiment, the kit containers may further include a pharmaceutically acceptable carrier. The kit may further include a sterile diluent, which is preferably stored in a separate additional container. In another embodiment, the kit further comprising a package insert comprising printed instructions directing the use of a combined treatment of a pH buffer and the anti-cancer agent as a method for treating tumors, tumor metastases, or other cancers in a patient. The kit may also comprise additional containers comprising additional anti-cancer agents, agents that enhances the effect of such agents, or other compounds that improve the efficacy or tolerability of the treatment.

As used herein, the term "patient" or "subject" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

In a preferred embodiment, the patient or subject is a human in need of treatment for cancer, or a precancerous condition or lesion, wherein the cancer is any type of cancer. Examples of cancers that may be treated by the methods described herein include but are not limited to: sarcomas, lung cancers, bone cancers, skin cancers, cancers of the head or neck, cutaneous or intraocular melanoma, uterine cancer, ovarian cancer, carcinoma of the vagina, carcinoma of the vulva, gastrointestinal cancers, cancers of the endocrine system, uroepithelial cancers, cancer of the penis, prostate cancer, mesothelioma, hepatocellular cancer, biliary cancer, cancer of the kidney, chronic or acute leukemia, lymphomas, neoplasms of the central nervous system, (CNS), squamous cell carcinomas, pancreatic adenocarcinoma, including refractory versions of any of the above cancers, or a combination of one or more of the above cancers.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

All references cited in the present application incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A recombinant myxoma virus that encodes the orfC gene of walleye dermal sarcoma virus (WDSV).

2. The recombinant myxoma virus of claim 1 wherein the orfC gene of walleye dermal sarcoma virus is inserted between M135 and M136 open reading frames of the myxoma virus genome.

3. The recombinant myxoma virus of claim 1 wherein the orfC gene of walleye dermal sarcoma virus is under the control of a late poxvirus promoter.

4. The recombinant myxoma virus of claim 1 wherein the myxoma virus is an attenuated myxoma virus.

5. A method of killing a cancer cell comprising contacting the cell with the recombinant myxoma virus of claim 1.

6. The method of claim 5, wherein the cell is a mammalian cancer cell.

7. The method of claim 5, wherein the cell is a human cancer cell.

8. The recombinant myxoma virus of claim 3 wherein the late poxvirus promoter is a p11 promoter.

* * * * *